United States Patent
Minerath, III et al.

(10) Patent No.: US 6,521,240 B1
(45) Date of Patent: *Feb. 18, 2003

(54) FACIAL TISSUE COMPOSITION FOR SEQUESTRATION OF NASAL SECRETION SKIN IRRITANTS

(75) Inventors: Bernard Joseph Minerath, III, Oshkosh, WI (US); Brenda Marie Nelson, Appleton, WI (US); David Roland Otts, Appleton, WI (US); Linda Susan Huard, Appleton, WI (US); David John Tyrrell, Appleton, WI (US); Gary Lee Shanklin, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,675

(22) Filed: Dec. 29, 1999

Related U.S. Application Data

(60) Provisional application No. 60/114,497, filed on Dec. 31, 1998, and provisional application No. 60/114,496, filed on Dec. 31, 1998.

(51) Int. Cl.[7] .......................... A01N 25/34; A61K 6/00; A61K 9/00; A61F 13/00
(52) U.S. Cl. ...................... 424/402; 424/401; 424/443; 424/400; 424/78.08
(58) Field of Search ................................. 424/443, 449, 424/405; 514/53

(56) References Cited

U.S. PATENT DOCUMENTS

| 144,315 A | 11/1873 | Cooper |
|---|---|---|
| 433,827 A | 8/1890 | Schultz |
| 795,562 A | 7/1905 | Tatti |
| 810,115 A | 1/1906 | Green |
| 1,098,176 A | 5/1914 | Schwerin |

(List continued on next page.)

FOREIGN PATENT DOCUMENTS

| DE | 2 260 612 | 9/1974 | .......... A47K/10/16 |
|---|---|---|---|
| DE | 3 924 898 | 1/1991 | .......... D21H/17/71 |
| EP | 365 726 | 5/1990 | .......... D21H/21/14 |
| EP | 609 301 | 8/1994 | ............ A61K/7/48 |
| EP | 0 699 446 A1 | 3/1996 | |

(List continued on next page.)

OTHER PUBLICATIONS

Frosch et al. 1994, Efficacy of Skin Barrier Creams (IV). The Repetitive Irritation Test (RIT) with a set of 4 Standard Irritants. *Contact Dermatitis.* 31:161–168.
Treffel et al. 1994. Evaluation of Barrier Creams: An in vitro Technique on Human Skin. *Acta Derm Venerol.* 74:7–11.
Malmsten. 1998. Formation of Adsorbed Protein Layers. *J. Colloid and Interface Sci.* 207:186–199.
Saaverda et al. 1988. The adsorption of Proteins on Chemically Modified Hydrophobic Surfaces. In Chemically Modified In Science and Industry: Proceedings of the Chemically Modified Surfaces Symposium (1987; Fort Collins, CO). Leyden, D. E. and Collins, W. T. eds. Gordon and Breach Science Publishers, New York, NY. pp. 67–77.

(List continued on next page.)

*Primary Examiner*—Thurman K. Page
*Assistant Examiner*—Isis Ghali
(74) *Attorney, Agent, or Firm*—Pauley Petersen Kinne & Erickson

(57) ABSTRACT

Facial tissue is provided comprising a tissue substrate, a hydrophilic nasal secretion skin irritant sequestering agent and a hydrophobic nasal secretion skin irritant sequestering agent. In one embodiment the sequestering agents are comprised of modified and non-modified clays. In one embodiment the skin irritants are bound to sequestering agents present on a substrate. In another embodiment the skin irritants are bound to sequestering agents present on the skin.

25 Claims, 9 Drawing Sheets

U.S. PATENT DOCUMENTS

| | | | |
|---|---|---|---|
| 1,634,974 A | 7/1927 | Bucci | |
| 1,900,973 A | 3/1933 | Bertsch | |
| 1,999,161 A | 4/1935 | Walton | 167/91 |
| 2,020,517 A | 11/1935 | Rewald | 8/6 |
| 2,137,310 A | 11/1938 | Sommer | 92/21 |
| 2,186,709 A | 1/1940 | Rowland | 92/21 |
| 2,317,908 A | 4/1943 | Grady | 167/14 |
| 2,523,316 A | 9/1950 | McClenahan et al. | 167/63 |
| 2,678,320 A | 5/1954 | Scharf | 252/354 |
| 2,684,321 A | 7/1954 | Thurmon et al. | 167/58 |
| 2,795,568 A | 6/1957 | Ruehrwein | 260/41 |
| 2,883,356 A | 4/1959 | Gluesenkamp | 260/37 |
| 2,944,931 A | 7/1960 | Yang | 162/179 |
| 2,999,265 A | 9/1961 | Duane et al. | 15/506 |
| 3,061,512 A | 10/1962 | Anderson, Jr. et al. | 167/58 |
| 3,069,361 A | 12/1962 | Cogswell | 252/363.5 |
| 3,208,984 A | 9/1965 | Dekking | 260/89.5 |
| 3,243,369 A | 3/1966 | Dekking | 252/28 |
| 3,264,188 A | 8/1966 | Gresham | 167/84 |
| 3,296,055 A | 1/1967 | Wilkins | 156/433 |
| 3,431,133 A | 3/1969 | Braude et al. | 117/24 |
| 3,594,221 A | 7/1971 | Baldwin | 117/138.5 |
| 3,619,280 A | 11/1971 | Scheuer | 117/154 |
| 3,935,363 A | 1/1976 | Burkholder et al. | 428/281 |
| 3,991,184 A | 11/1976 | Kludas et al. | 424/177 |
| 4,178,254 A | 12/1979 | Leikhim et al. | 252/8.6 |
| 4,344,967 A | 8/1982 | Easton et al. | 424/359 |
| 4,379,863 A | 4/1983 | Snyder | 423/105 |
| 4,450,151 A | 5/1984 | Shinozawa | 424/46 |
| 4,454,159 A | 6/1984 | Musher | 424/358 |
| 4,463,017 A | 7/1984 | Hidalgo et al. | 424/359 |
| 4,556,560 A | 12/1985 | Buckingham | 424/145 |
| 4,559,157 A | 12/1985 | Smith et al. | 252/90 |
| 4,637,933 A | 1/1987 | Zabotto et al. | 424/131 |
| 4,657,537 A | 4/1987 | Zimmerer | 604/360 |
| 4,685,909 A | 8/1987 | Berg et al. | 604/360 |
| 4,707,293 A | 11/1987 | Ferro | 252/174.17 |
| 4,717,735 A | 1/1988 | Strem | 424/447 |
| 4,784,986 A | 11/1988 | Usher | 514/2 |
| 4,847,089 A | 7/1989 | Kramer et al. | |
| 4,857,308 A | 8/1989 | Fukasawa et al. | 424/63 |
| 4,861,584 A | 8/1989 | Powell, Jr. et al. | 424/79 |
| 4,894,222 A | 1/1990 | Matravers | 424/59 |
| 4,943,350 A | 7/1990 | Bogart et al. | 162/158 |
| 5,017,361 A | 5/1991 | Powell, Jr. et al. | 424/46 |
| 5,109,533 A | 4/1992 | Mine et al. | 455/63 |
| 5,122,418 A | 6/1992 | Nakane et al. | 424/401 |
| 5,190,533 A | 3/1993 | Blackburn | 604/367 |
| 5,194,261 A | 3/1993 | Pichierri | 424/401 |
| 5,232,691 A | 8/1993 | Lemole | 424/78.02 |
| 5,306,444 A | 4/1994 | Kitamura et al. | 252/546 |
| 5,362,488 A | 11/1994 | Sibley et al. | 424/78.05 |
| 5,434,183 A | 7/1995 | Larsson-Blackström | 514/549 |
| 5,508,034 A | 4/1996 | Bernstein | 424/401 |
| 5,519,060 A | 5/1996 | Sprengeler et al. | 514/601 |
| 5,611,890 A | 3/1997 | Vinson et al. | 424/401 |
| 5,612,307 A | 3/1997 | Chambers et al. | 510/406 |
| 5,618,529 A | 4/1997 | Pichierri | 424/78.06 |
| 5,631,012 A | 5/1997 | Shanni | 424/401 |
| 5,637,616 A | 6/1997 | Sharpe et al. | 514/562 |
| 5,641,483 A | 6/1997 | Beaulieu | 424/78.06 |
| 5,643,899 A | 7/1997 | Elias et al. | 514/171 |
| 5,658,559 A | 8/1997 | Smith | 424/78.02 |
| 5,672,248 A | 9/1997 | Wendt et al. | 162/109 |
| 5,700,352 A | 12/1997 | Vinson et al. | 162/111 |
| 5,702,709 A | 12/1997 | Schulz et al. | 424/401 |
| 5,714,154 A | 2/1998 | Le Hen-Ferrenbach et al. | 424/401 |
| 5,720,832 A | 2/1998 | Minto et al. | 156/62.4 |
| 5,720,966 A | 2/1998 | Ostendorf | 424/402 |
| 5,738,856 A | 4/1998 | Korb et al. | 424/401 |
| 5,738,859 A | 4/1998 | Posner | 424/401 |
| 5,759,346 A | 6/1998 | Vinson | 162/123 |
| 5,763,332 A * | 6/1998 | Gordon et al. | |
| 5,830,317 A | 11/1998 | Vinson et al. | 162/125 |
| 5,869,033 A | 2/1999 | Schulz | 424/78.02 |
| 5,908,836 A * | 6/1999 | Bar-Shalom et al. | |
| 5,945,409 A | 8/1999 | Crandall | 514/78 |
| 5,951,991 A | 9/1999 | Wagner et al. | 424/401 |
| 5,958,185 A | 9/1999 | Vinson et al. | 162/111 |
| 6,001,377 A | 12/1999 | SaNogueria, Jr. et al. | 424/401 |
| 6,015,574 A | 1/2000 | Cannell et al. | 424/450 |
| 6,030,675 A * | 2/2000 | Schroeder et al. | |
| 6,049,915 A | 4/2000 | Malowaniec | 2/400 |
| 6,051,749 A | 4/2000 | Schulz | 604/368 |
| 6,066,673 A | 5/2000 | Mellver et al. | 514/634 |

FOREIGN PATENT DOCUMENTS

| | | | |
|---|---|---|---|
| EP | WO 97/38735 | * 10/1997 | |
| EP | 0 811 389 A1 | 12/1997 | |
| EP | 0 937 467 A1 | 8/1999 | |
| GB | 1 327 041 | 8/1973 | D21J/7/00 |
| GB | 2 115 702 A | 2/1983 | |
| JP | 4011-313 | 6/1977 | |
| JP | 8220-896 | 6/1982 | |
| JP | 62-250038 | 10/1987 | C08J/9/00 |
| JP | 62-254841 | 11/1987 | B01L/20/26 |
| JP | 63-192703 | 8/1988 | A61K/7/48 |
| JP | 3008-897 | 8/1989 | |
| JP | 1-221575 | 9/1989 | D06M/15/263 |
| JP | 2-057252 | 2/1990 | A61K/13/15 |
| JP | 2-200607 | 8/1990 | A61K/7/00 |
| JP | 2-264078 | 10/1990 | A61F/5/44 |
| JP | 4-082824 | 3/1992 | A61K/7/00 |
| JP | 4-272296 | 9/1992 | |
| JP | 4-273809 | 9/1992 | A61K/00/00 |
| JP | 6-080547 | 3/1994 | A61K/7/48 |
| JP | 6-345633 | 12/1994 | A61K/7/48 |
| JP | 7-069827 | 3/1995 | A61K/7/00 |
| JP | 7-316444 | 12/1995 | C08L/101/14 |
| JP | 8-047509 | 2/1996 | A61K/13/54 |
| JP | 8-119846 | 5/1996 | A61K/7/48 |
| JP | 409087687 A | 3/1997 | |
| JP | 9-136836 | 5/1997 | A61K/31/215 |
| JP | 9-302138 | 11/1997 | C08K/3/22 |
| JP | 10-175843 | 6/1998 | |
| SU | 1781355 | 4/1990 | |
| WO | 81/01643 | 6/1981 | A41B/13/02 |
| WO | 96/28139 | 9/1996 | A61K/7/50 |
| WO | 97/17494 | 5/1997 | D21H/27/40 |
| WO | 97/31153 | 8/1997 | D21H/21/24 |
| WO | 97/42934 | 11/1997 | A61K/7/48 |
| WO | 97/44008 | 11/1997 | A61K/7/40 |
| WO | 98/13549 | 4/1998 | D21H/25/00 |
| WO | 98/17856 | 4/1998 | D21C/9/00 |
| WO | 98/28491 | 7/1998 | D21H/17/67 |
| WO | 98/34589 | 8/1998 | A61K/7/48 |
| WO | WO 98/55096 | 12/1998 | |
| WO | WO 99/21532 | 5/1999 | |
| WO | 99/26610 | 6/1999 | A61K/31/00 |
| WO | WO 99/45973 | 9/1999 | |
| WO | 99/45974 | 9/1999 | A61L/15/44 |
| WO | 99/46316 | 9/1999 | C08G/65/48 |

OTHER PUBLICATIONS

Tombacz et al. 1988. Surface Modification of Clay Minerals by Organic Polyions. *Colloids and Surfaces A: Physiochemical and Eng. Aspects.* 141:379–384.

Sullivan et al. 1998. Thermodynamics of Cationic Surfactant Sorption onto Natural Clinoptilolite. *J. Colloid & Interface Sci.* 206:369–380.

Biasci et al. 1994. Functionalization of Montmorillonite by Methyl Methacrylate Polymers Containing Side Chain Ammonium Cations. *Polymer.* 35(15):3296–3309.

Kamyshny, A., Toledano, O., and Magdassi, S. 1999. Adsorption of Hydrophobized IgG and Gelatin onto Phosphatidyl Choline–coated Silica. Colloids and Surfaces B: Biointerfaces 13:187–194.

Atun et al. 1998. Adsorption of Safarine–O on Hydrophilic and Hydrophobic Glass Surfaces. *Colloids and Surfaces A: Physiochemical and Eng. Aspects.* 143:27–33.

Parida et al. 1998. Adsorption of Styryl Pyridinium Dyes on Polyethylene–glycol–treated Silica. *Colloids and Surfaces A: Physiochemical and Eng. Aspects.* 134:249–255.

Markowitz et al. 1999. Surface Acidity and Basicity of Functionalized Silica Particles. *Colloids and Surfaces A: Physiochemical and Eng. Aspects.* 150:85–94.

Kandori et al. 1999. Adsorption of Bovine Serum Albumin and Lysozyme on Hydrophobic Calcium Hydroxyapatites. *J. Colloid & Interface Sci.* 212:600–603.

Kandori et al. 1999. Preparation and Characterization of Hydrophobic Calcium Hydroxyapatite Particles Grafting Oleylphosphate Groups. *Colloids and Surfaces A: Physiochemical and Eng. Aspects.* 150:161–170.

Esumi et al. 1998. Adsorption Characteristics of Cationic Surfactants on Titanium Dioxide with Quaternary Ammonium Groups and Their Adsolubilization. *J. Colloid & Interface Sci.* 202:377–384.

Sato, J. et al 1998. *Cholesterol Sulfate Inhibits Proteases that are Involved in Desquamation of Stratum Corneum,* The Journal of Investigative Dermatology, pp. 189–193.

Journal of Applied Toxicology, 1996, vol. 16(1), Summary of pages 65–70.

Turner, R. B. et al. 1998. Association Between Interleukin–8 Concentration in Nasal Secretions and Severity of Symptoms of Experimental Rhinovirus Colds. Clin. Infect. Dis. 26–840–846.

Roseler, S. et al. 1995. Elevated levels of Interleukins IL–1β, IL–6, and IL–8 in Naturally Acquired Viral Rhinitis. Eur. Arch. Otolaryn. 252 (Sppl. 1):S61–S63.

Bachert, C. et al. 1995. Proinflammatory Cytokines in Allergic Rhinitis. Eur. Arch. Otolaryn, 252 (Suppl. 1):S44–S49.

Baumgarten, W. J–A. and Petersson, G. 1995. Contralateral Differences Among Biomarkers Determined by a Modified Nasal Lavage Technique after Unilateral Antigen Challenge. Allergy 50:308–315.

Howarth, P. H. 1997. Mediators of Nasal Blockage in Allergic Rhinitis. Allergy, 52 (Suppl. 40):12–18.

Smitz, W.D. et al 1997. An Approach to the Understanding of the Nasal Early–Phase Reaction Induced by Nasal Allergen Challenge. Allergy, 52:162–167.

Togias, A. G. et al 1985. Nasal Challenge with Cold, Dry Air Results in Release of Inflammatory Mediators. J. Clin. Invest. 76:1375–1381.

Knapp, H. R. and Murray, J. J. 1994. Leukotrienes as Mediators of Nasal Inflammation. Adv. Prostaglandin, Thromboxane, and Leukotriene Research, 22:279–288.

Short, S. M. 1995. Transport of Biological Active Interferon–gamma Across Human Skin In Vitro Pharm. Res. 12(8):1140–1145.

Greaves, M. W. and Camp. R. D. R. 1988. Prostaglandins, Leukotrienes, Phospholipase, Platelet Activating Factor and Cytokines: An Integrated Approach to Inflammation of Human Skin. Arch. Dermatol. Res. 280 (Suppl.):S33–S41.

Strange, P. et al., 1996. Staphylococcal Enterotoxin B Applied on Intact Normal and Intact Atopic Skin Induces Dermatitis. Arch. Dermatol. 132:27–33.

Schaefer, H. and Redelmeier, T. E. 1996. Relationship Between the Structure of Compounds and Their Diffusion Across Membranes, pp. 87–117. In Skin Barrier: Principles of Percutaneous Absorption.Karger, AG. Basel, Switzerland.

Distante, F. and Berardesca,E. 1995. Transepidermal Water Loss, pp. 1–4. In E. Berardesca (ed.), Bioengineering of the Skin: Methods of Instrumentation. CRC Press, Inc., Boca Raton, FL.

Rougier, A., Lotte, C. and Mailbach, H. 1989. In vivo Relationship Between Percutaneous Absorption and Transepidermal Water Loss, pp. 175–190. In Bronaugh, R.L. and Maibach, H. I. (eds.), Percutaneous Absorption: Mechanisms–Methodology–Drug Delivery (2d ed.). Marcel Dekker, Inc., New York, NY.

Lopez, S. et al. 1998. Profile of Women's Facial Skin for Transepidermal Water Loss, Temperature and Sebum Causal Level. Poster presented at the 12th International Symposium on Bioengineering and the Skin. Boston, Jun. 25–27, 1998.

Wester, R. and Maibach, H. I. 1989. Regional Variation in Percutaneous Absorption, pp. 111–119. In Bonaugh, R. L. and Maibach, H. I. (eds.), Percutaneous Absorption: Mechanisms–Methodology–Drug Delivery (2nd ed.). Marcel Dekker, Inc., New York, NY.

Taljebini, M. et al. 1996 Cutaneous Permeability Barrier Repair Following Various Types of Insults: Kinetics and Effects of Occlusion. Skin Pharmacol. 9:111–119.

Ueda, H. et al, 1996. Change in the Electrochemical Properties of Skin and the Lipid Packing in Stratum Corneum by Ultrasonic Radiation. Int. J. Pharm. 137:217–224.

Pliquett, U. and Weaver C. 1996. Electroporation of Human Skin: Simultaneous Measurement of Changes in the Transport of Two Fluorescent Molecules and in the Passive Electrical Properties. Bioelectrochem. and Bioenerget. 39:1–12.

Patil, S., et al., 1996. Epidermal Enzymes as Penetration Enhancers in the Transdermal Drug Delivery. J. Pharm. Sci. 85(3):249–252

Menon, G. K., Feingold, K.R. and Elias, P. M. , 1992. Lamellar Body Secretory Response to Barrier Disruption. J. Invest. Dermatol. 98:279–289.

Leveque, J. L. et al., 1993. How does Sodium Lauryl Sulfate Alter the Skin Barrier Function in Man? A Multiparametric Approach. Skin Pharmacol. 6:111–115.

Denda, M. et al., 1998. Exposure to a Dry Environment Enhances Epidermal Permeability Barrier Function. J. Invest. Dermatol. 111:858–863.

Frosh, P. J. and Kurte, A. 1994. Efficacy of Skin Barrier Creams (IV). The Repetitive Irritation Test (RIT) with a set of 4 Standard Irritants. Contact Dermatitis 31:161–168.

Treffel, P., Gabard, and Juch, R. 1994. Evaluation of Barrier Creams: An In vitro Technique on Human Skin. Acta Derm Venerol 74:7–11.

* cited by examiner

Sequestration of LTB4 from Nasal Secretions by Clays

FIG. 13

Sequestration of PGE2 from Nasal Secretions by Clays

FIG. 14

FACIAL TISSUE COMPOSITION FOR SEQUESTRATION OF NASAL SECRETION SKIN IRRITANTS

CROSS-RELATION TO PRIOR APPLICATIONS

The present application claims priority to U.S. Provisional Application Nos. 60/114,497 and 60/114,496 both filed on Dec. 31, 1998.

BACKGROUND OF THE INVENTION

The stratum corneum is the superficial cornified layer of the skin that provides a barrier to water evaporation and, as such, is essential for terrestrial life. In addition to preventing water loss, the stratum corneum also reduces the permeation of undesirable molecules from the external environment. The stratum corneum consists of dead cells (corneocytes) embedded in a lipid-rich (fatty-acid, ceramide, cholesterol) matrix. Both the corneocytes and the intracelluar lipids are derived from epidermal keratinocytes. This structure of corneocytes embedded in lipids has given rise to a brick (corneocytes) and mortar (lipids) model of stratum corneum structure and function. It is thought that much of the barrier properties of the skin can be attributed to this structure. Substances deposited on the skin must traverse this structure through a tortuous path to gain access the underlying viable layers of the skin. Substances that are irritating to the skin often initiate an elaborate cascade of immunological events once they contact viable skin cells. These events ultimately lead to skin inflammation.

Nasolabial skin is more vulnerable to skin irritation than many other sites on the body. This vulnerability is due to the decreased barrier function of nasolabial skin relative to other body sites. The rate of water loss through the skin can be measured and is indicative of the barrier properties of the skin[12]. A low level of water loss through the skin is normal. Movement of water through the skin is often referred to as Transepidermal Water Loss (TEWL) and is typically expressed as $g \cdot M^{-2} \cdot hr^{-1}$. TEWL readings are routinely used to determine the barrier properties of a skin site at any given point in time[13]. Normally, significant differences in TEWL values can be found between disparate anatomical sites[14]. Studies have shown that the barrier properties of facial skin are significantly lower than other sites on the body. Indeed, differences in barrier properties between various sites on the face itself have been observed[14,15]. Indeed, the TEWL values obtained for nasolabial skin were among the highest values obtained on the face. With few exceptions, it appears that the face, and more specifically, nasolabial skin, has the lowest barrier properties of any skin site on the human body.

The barrier function of the skin with regard to moisture barrier, as measured by TEWL, often correlates with the skin's ability to exclude exogenous substances as well[14,16]. As the barrier to water decreases (increasing TEWL value) exogenously applied molecules are often more likely to penetrate to the viable layers of the skin[12]. This suggests that nasolabial skin may be more permeable to topically applied irritants and therefore more susceptible to inflammation relative to other skin sites.

Skin barrier function can be compromised by a variety of insults. Examples of treatments known to diminish skin barrier function include, but are not limited to, physical treatments (abrasion, tape stripping, ultrasonics, electrical fields), enzymes, solvents, surfactants, and elevated ambient humidity[17,18,19,20,21,22,23]. Repeated wiping of nasolabial skin with facial tissue can diminish skin barrier function due to abrasion. Insults that diminish skin barrier function can predispose skin to inflammatory events by the enhanced uptake of irritants through the stratum corneum.

The nasal secretions of individuals experiencing colds or allergies contain a myriad of substances that can potentially irritate nasolabial skin. These substances include but are not limited to, an array of biologically active components including cytokines, eicosanoids, enzymes, and various toxins. For example, the cytokines interleukin-1β (IL-1β) and interleukin-8 (IL-8) are present in high concentrations in nasal secretions[1,2,3]. Likewise, the eicosanoids leukotriene $B_4$ ($LTB_4$) and prostaglandin $E_2$ ($PGE_2$) are also present at high concentrations in nasal secretions[4,5,6,7,8]. Additionally, the enzymes kinase, tryptase, phospholipase, and glycosydase are present in nasal secretions. Finally, nasal secretions can contain superantigens produced by the bacterium *Staphylococcus aureus* including staphylococcal enterotoxins A (SEA), B (SEB), and Toxic Shock Syndrome Toxin-1 (TSST-1) as well as other bacterial by-products. Furthermore, the cutaneous responses to topically applied cytokines, eicosanoids, enzymes, and superantigens have also been described[9,10,11].

Therefore, nasal secretions contain a variety of irritants that during a cold or allergy event can initiate skin inflammation. These irritating substances are deposited on nasolabial skin, a site that normally has low barrier properties. The barrier properties of this anatomical site can be further diminished by the repeated use of facial tissue, a normal practice during episodes of allergies and colds. The result is a red and sore nose, a common symptom experienced by cold and allergy sufferers.

Many unrelated avenues of research exist regarding the composition of nasal secretions, the skin's response to various components present in nasal secretions, and the barrier attributes of nasolabial skin. Despite the existence of these unrelated areas of research, it is surprising that the concept of nasal secretion mediated skin irritation has not been described. Consequently, the art is devoid of any technology to specifically address this novel cause for a common form of skin irritation. What is absent in the art today are novel mechanisms for preventing or mitigating skin inflammation due to the exceedingly complex mixture of irritants in nasal secretions.

A number of approaches are known for protecting the skin against the action of skin irritants. Examples include protective apparel, skin protectant formulations, and anti-inflammatory compositions.

The use of protective apparel is a highly efficacious means of preventing irritants from coming in contact with the skin. However, even if such a garment was available, this approach has little chance of gaining widespread consumer acceptance for use on nasolabial skin.

Barrier compositions can provide demonstrable clinical benefits. However, it is known that while many compositions can retard the penetration of one type of irritant it may not afford a similar level of protection against others[24,25]. This evidence suggests that many currently available skin protectant formulations are unable to exclude a wide range of irritants that differ based on hydrophobicity, size, and/or chemical composition. Consequently, many skin protectant formulations may not provide adequate protection against biological fluids that contain a complex mixture of skin irritants.

Another method of addressing skin irritation due to contact with skin irritants is the use of anti-inflammatory compounds. The topical use of anti-inflammatory compounds does not protect the skin from coming in contact with an irritant. Instead, for many skin irritants, damage to the skin still occurs but the inflammatory response is mitigated by the anti-inflammatory substance. Therefore, the effect of anti-inflammatory compounds is exerted by influencing the biology of viable skin cells rather than by preventing the skin damage that elicits the inflammatory event in the first place.

PCT publication WO 97/38735 teaches the use of a singular sequestrant (organophilic clays; clays modified with hydrophobic substances), such as quarternium-18 bentonite, to absorb and deactivate fecal proteolytic enzymes to prevent diaper rash of the skin. A diaper fabric incorporating the organophilic clay dispersed in a super absorbent polymer is suggested, as well as other pharmaceutically suitable vehicles for the organophilic clay, such as lotions, emulsions, creams, gels, and aqueous vehicles. The reference teaches that compounds having C-8 and longer hydrocarbon chains should be excluded from the composition. The protective composition is specifically intended to act as a barrier to prevent fecal enzymes from contacting the skin. Further, lotions and aerosols containing organophilic clay, ion exchanged with a quaternary ammonium compound, are used to block and absorb plant allergens in U.S. Pat. Nos. 5,017,361 and 5,702,709. Additionally, art exists to describe the inclusion of non-modified clays into tissue products for purposes unrelated to skin health (U.S. Pat. Nos. 5,611,890 and 5,830,317).

Skin protectants that augment skin barrier properties to thwart the penetration of exogenous irritants can have skin health benefits. Various technological approaches to deliver these benefits are known to those skilled in the art. It is the object of this invention to provide novel compositions and methods necessary to protect nasolabial skin from the skin irritants present in nasal secretions. Thus, this invention provides for novel approaches to mitigate a common source of skin irritation.

What is needed in the art are novel mechanisms to promote skin health.

What is needed in the art are novel mechanisms to promote nasolabial skin health.

What is needed in the art are novel mechanisms to mitigate or prevent nasolabial skin irritation and inflammation due to the topical deposition of skin irritants present in nasal secretions. Novel approaches are needed as many of the skin irritants present in nasal secretions are unique to this biological fluid.

Thus, the present invention provides that skin inflammation can be caused by the penetration of inflammatory agents present in nasal secretions through the stratum corneum and into the underlying viable layers of the skin. For example, biologically active cytokines, eicosanoids, enzymes, and superantigens can permeate through the stratum corneum to the viable layers of the skin and elicit undesirable biological effects including skin inflammation. The concept of nasal secretion mediated skin inflammation has not been described until now. Therefore, the invention described herein provides for novel compositions and methods to help prevent undesirable skin symptoms caused by the deposition of nasal secretions on nasolabial skin.

SUMMARY OF THE INVENTION

The present invention provides compositions to prevent the penetration of skin irritants through the stratum corneum into the viable layers of the skin. The present invention provides compositions for protecting against nasal secretion mediated skin inflammation. Thus, the present invention provides compositions for promoting improved nasolabial skin health.

One embodiment of the present invention is directed to a facial tissue comprising a tissue substrate containing (a) sequestrant(s) with an affinity for skin irritants present in nasal secretions. One embodiment of the invention provides for a tissue substrate containing (a) sequestrant(s) for hydrophobic skin irritants present in nasal secretions. Another embodiment of the invention provides for a tissue substrate containing (a) sequestrant(s) for hydrophilic skin irritants present in nasal secretions. In an alternate embodiment, the invention is directed toward a facial tissue comprising a tissue substrate containing (a) sequestrant(s) with an affinity for hydrophobic skin irritants present in nasal secretions and (a) sequestrant(s) with an affinity for hydrophilic irritants present in nasal secretions.

In another embodiment, the hydrophilic and hydrophobic skin irritant sequestering agents are isolated from each other in discrete regions of the tissue substrate.

In a further embodiment, the discrete regions of the substrate are defined by the hydrophilic and hydrophobic sequestering agents each being present on separate plies and/or layers of a given ply of the substrate.

In a further embodiment, the discrete regions of the substrate are defined by a pattern configuration wherein the hydrophilic and hydrophobic sequestering agents are each relegated to separate regions of the pattern on the substrate.

In a further embodiment, the discrete regions of the substrate are defined by the hydrophilic and hydrophobic sequestering agents each being present on separate fibers of the substrate. These fibers may be coated or filled with the sequestrant material(s). The aforementioned fibers may comprise all or a fraction of the total fibers used to make the tissue substrate.

The substrate used in the present invention can be prepared from a variety of materials. Suitable materials comprise any matter that does not hinder the sequestering agents' affinity for binding nasal secretion skin irritants. One example of a suitable substrate is a tissue prepared from plant fibers.

To be effective, sequestering agents must bind skin irritants present in nasal secretions. Examples of skin irritants present in nasal secretions include, but are not limited to, cytokines (such as interleukin-1α, IL-1β and IL-8), eicosanoids (such as $PGE_2$ and $LTB_4$), and superantigens (such as those produced by the bacterium *Staphylococcus aureus* including staphylococcal enterotoxins A, B, and Toxic shock syndrome toxin-1). The examples of skin irritants listed above are not intended to represent an exhaustive list of factors present in nasal secretions that are irritating to the skin, rather, they are incorporated to aid in illustrating the utility of the invention. Certain embodiments of the present invention include facial tissue comprising both hydrophilic and hydrophobic sequestering agents having an affinity for binding the irritants listed above.

The sequestering agents could be any material(s) capable of binding skin irritants present in nasal secretions. Examples of suitable sequestering agents include, but are not limited to, modified and non-modified clay, modified and non-modified silica, modified and non-modified $TiO_2$, and modified and non-modified refractory metal oxides. The invention provides that hydrophilic skin irritants, such as cytokines, bind to hydrophilic sequestering agents, such as non-modified clay for example. Likewise, the invention provides that those hydrophobic skin irritants, such as eicosanoids, bind to hydrophobic sequestering agents, such as modified clay for example.

Sequestering agents can be imparted to the skin's surface via a substrate (for example a facial tissue) and then removed by normal desquamatory events (normal sloughing of the outermost layer of the skin) and/or personal hygiene. The transfer of sequestering agents from the substrate to the skin can be accomplished via any number of suitable vehicles including, but not limited to, anhydrous formulations, gels, pastes, creams, powders, lotions, emulsions, or aqueous formulations or any combination thereof.

Alternatively, sequestering agents may remain bound to a facial tissue to minimize their interaction with the skin. In this case, the irritants are removed from the skin by binding to one or more sequestrants present on a facial tissue. It is understood that these two distinct modes of action (binding irritants to sequestrants deposited on the skin's surface or binding irritants to sequestrants present on facial tissue and therefore removing the irritants from the skin's surface to a facial tissue) are not mutually exclusive and can be combined.

BRIEF DESCRIPTION OF THE DRAWINGS

FIG. 13 shows the ability of both derivatized and non-modified clays to bind the skin irritant $LTB_4$ from human nasal secretions.

FIG. 14 shows the ability of both derivatized and non-modified clays to bind the skin irritant $PGE_2$ from human nasal secretions.

DETAILED DESCRIPTION OF THE INVENTION

Figure 1:
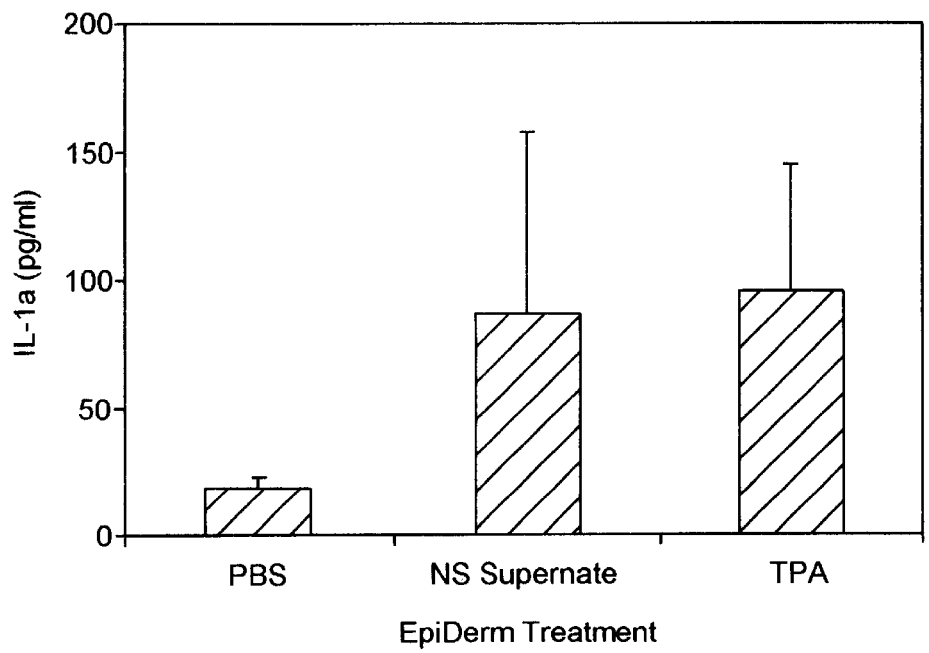
FIG. 1 shows a pro-inflammatory response (accumulation of IL-1α) occurs when nasal secretions are applied to a living human skin model.

The present invention provides compositions for sequestering inflammatory agents present in nasal secretions to improve nasolabial skin health. Binding skin irritants present in nasal secretions to sequestrants deposited on the surface of the skin (the stratum corneum) thwarts irritant penetration to underlying skin layers to prevent skin irritation. Sequestrants with bound skin irritants are removed from the skin through the normal process of desquamation and/or personal hygiene. This benefit may also be realized by using a tissue having the sequestering agent bound thereto. The sequestering agent is in some embodiments of sufficient size or charge to prevent the penetration of skin irritants into the viable skin layers due to steric hindrance and/or charge exclusion.

The present invention is directed to a facial tissue containing nasal secretion skin irritant sequestering agents and to a method of using the facial tissue to sequester nasal secretion skin irritants. The facial tissue contains both hydrophilic and hydrophobic nasal secretion skin irritant sequestering agents. In one embodiment, the hydrophilic and hydrophobic sequestering agents are spatially isolated from each other by being present in different regions of the facial tissue. This spatial isolation by region can be accomplished in many different ways.

In one embodiment of the present invention, the hydrophilic and hydrophobic sequestering agents are separated by region wherein the hydrophilic and hydrophobic sequestering agents are physically located in discrete areas of the facial tissue. For example, the hydrophilic agent and hydrophobic agent could each be relegated to one half of the facial tissue or an increasingly complex pattern of distinct regions, e.g. quilted, dots or grid. The well-known facial tissue manufacturing technique of printing or slot application can be used to impart hydrophobic and/or hydrophilic sequestering agents to a facial tissue in the present invention. It is understood that there may be some overlap between hydrophobic and hydrophilic sequestering agent regions, however at least some regions containing only one or the other type of sequestering agents are contemplated in this embodiment.

In another embodiment, the hydrophilic and hydrophobic sequestering agents are separated by region wherein each is located on separate layers or surfaces of the facial tissue. In a further embodiment, the hydrophilic and hydrophobic sequestering agents are separated by region, wherein a region is defined by the hydrophilic and hydrophobic sequestering agents being located on separate fibers within the substrate.

As used herein, the term "sequestering agent" or "sequestrant" means a material with an affinity for an irritant (biological or otherwise) such that the irritant covalently or non-covalently binds to the sequestrant when in the proximity of the sequestrant. In certain embodiments, the affinity for the irritant is high, rapid, and irreversible. Irritant interaction with the sequestrant should preclude or significantly diminish the ability of a target irritant to penetrate the stratum corneum to achieve access to the underlying viable layers of the skin.

As used herein, the term "sequestration" means the binding of an irritant to a sequestrant. Sequestration can be achieved using many well-known affinity ligand systems, such as adsorbent clays, calcium carbonate, talc, silica, refractory metal oxides, titanium dioxide ($TiO_2$), hydroxyapatite, alumina, aluminum silicate surfactants, calcium silicate, activated carbon, pearl starch, calcium sulfate, antibodies, ion-exchange materials, cyclodextrins, lectins, Lewis acid/base materials, activated charcoal, glass microspheres, diatomaceous earth reactions, derivatives and/or combinations of the above.

Native, unmodified, hydrophilic sequestering agents (such as clays, silicas, refractory metal oxides and $TiO_2$, for example) can be used for binding relatively charged proteinaceous irritants. Sequestering agents, such as clays existing in their natural state, or that have not had their net charge significantly altered by chemical means from their native state are termed herein as "unmodified." An unmodified clay is charged and therefore hydrophilic. Unmodified clays, such as bentonite, are particularly useful for sequestering irritants such as proteinaceous, hydrophilic inflammatory agents like the cytokines (i.e.: IL-8).

The invention provides that due to the presence of hydrophobic skin irritants, such as eicosanoids in nasal secretions, it is useful to modify certain sequestrants by increasing their hydrophobicity. Hydrophobic sequestering agents, such as clays that have had their net charge significantly altered by chemical means from their native state are termed herein as "modified." This hydrophobic modification of native sequestrants (such as clays, silicas, and $TiO_2$, for example) is preferred for binding relatively hydrophobic inflammatory agents such as eicosanoids. For example, a modified sequestrant shown here to be useful for sequestering eicosanoids ($PGE_2$ and $LTB_4$) present in nasal secretions, is a bentonite modified with a quarternary ammonium compound.

In certain embodiments, the invention provides that both hydrophilic and hydrophobic nasal secretion irritant sequestering agents are present on a facial tissue. The relative proportion of hydrophobic and hydrophilic skin irritants present in bodily fluids and the surrounding environment varies greatly from person to person. Although not wishing to be bound by theory, it is generally believed that hydrophilic skin irritants are present in a greater amount as measured by total irritant weight than are hydrophobic skin irritants.

Accordingly, the relative proportion and location of hydrophobic and hydrophilic sequestering agents present on facial tissue may also vary. In certain embodiments, approximately 1 part hydrophobic sequestering agent to approximately 100 parts hydrophilic sequestering agent by weight, or approximately 1 part hydrophobic sequestering agent to approximately 20 parts hydrophilic sequestering agent by weight, or approximately 1 part hydrophobic sequestering agent to approximately 1 part hydrophilic sequestering agent by weight may be used. Likewise, hydrophobic sequestering agents may be present in a greater amount than hydrophilic sequestering agents. Therefore, in certain embodiments, approximately 1 part hydrophilic sequestering agent to approximately 100 parts hydrophobic sequestering agent by weight, or approximately 1 part hydrophilic sequestering agent to approximately 20 parts hydrophobic sequestering agent by weight may be used.

As used herein, the term "nasal secretion irritant" means any component of nasal secretion that can inflame the nasolabial skin by penetrating the stratum corneum of the skin and therefore reaching the viable underlying layers. Additionally, substances that degrade one or more components of the stratum corneum are also considered to be skin irritants for the purposes of the invention described herein. Examples of skin irritants present in nasal secretions include, but are not limited to, cytokines (such as interleukin-1α, IL-1β and IL-8), eicosanoids (such as $PGE_2$ and $LTB_4$), enzymes (such as chymase, kinase, tryptase, phospholipase, and glycosidase), and superantigens (such as those produced by the bacterium *Staphylococcus aureus* including staphylococcal enterotoxins A, B, and Toxic shock syndrome toxin-1).

As used herein, the term "nasal skin" means the skin of the nose and area immediately surrounding the nose. As used herein, the term "nasolabial skin" is a broader term than nasal skin. It encompasses nasal skin as well as the area between the lips and distal portion of the nares.

As used herein, the term "hydrophilic" describes a material that has an affinity for charged nitrogenous molecules that are cationic, anionic, or amphiphilic. Further, the term "hydrophilic sequestering agent" describes a sequestering agent that has a greater affinity for hydrophilic skin irritants than do hydrophobic sequestering agents and/or paper fibers alone. Examples of irritants that can be bound by hydrophilic sequestering agents include, but are not limited to, proteinaceous skin irritants such as the cytokines, IL-8, interleukin-1α and interleukin-1β.

As used herein, the term "hydrophobic" describes a material that attracts lipid-derived molecules or molecules with significant. regions of hydrophobicity. Further, the term "hydrophobic sequestering agent" describes a sequestering agent that has a greater affinity for hydrophobic skin irritants than do hydrophilic sequestering agents and/or paper fibers alone. Examples of hydrophobic skin irritants relevant to nasal secretions that can be bound by hydrophobic sequestering agents include, but are not limited to, lipid derived skin irritants such as the eicosanoids, $LTB_4$ and $PGE_2$.

As used herein, the term "substrate" means a material suitable for carrying sequestering agents. The substrate may include a vehicle to facilitate delivering sequestrants to the skin's surface. Examples of suitable substrates include, but are not limited to, woven or non-woven materials that can include paper or fabric facial tissue. There are numerous suitable vehicles for facilitating the delivery of sequestering agents to the skin. A suitable vehicle is any material that can encounter the skin to deliver the sequestrants to the skin. Examples of suitable vehicles include, but are not limited to, anhydrous formulations, aqueous solutions, lotions, creams, pastes and the like.

In certain embodiments of the present invention, it is desireable to combine hydrophobic and hydrophilic sequestering agents, such as modified and non-modified clays, with lipophilic sequestering agent compositions. For example, unmodified clay in combination with various lipophilic sequestering agent compositions demonstrates a synergism resulting in additional sequestering affinity for nasal secretion skin irritants. As used herein "lipophilic sequestering agent composition" describes any substance that has a higher affinity for oil over water and provides a skin health benefit by directly interacting with the skin. Suitable examples of such benefits include, but are not limited to, enhancing skin barrier function, enhancing moisturization and nourishing the skin.

The lipophilic sequestering agent compositions may include stearic acid, isoparrafin, petrolatum, and a combination thereof. The lipophilic sequestering agent compositions can also be selected from fatty acids, fatty acid esters, fatty alcohols, triglycerides, phospholipids, mineral oils, essential oils, sterols, sterol esters, emollients, waxes, and a combination thereof In some embodiments, the lipophilic skin health benefit agent has an average hydrocarbon chain with length greater than eight carbons (C-8). An example of a lipophilic skin health benefit lotion composition is commercially available as Vaseline® Intensive Care Lotion (Chesebrough-Pond's, Inc.).

As used herein, suitable lipophilic sequestering agent compositions include, but are not limited to, the following materials classified according to CTFA designations:

Fats and Oils: Apricot Kernel Oil, Avocado Oil, Babassu Oil, Borage Seed Oil, Butter, $C_{12}$–$C_{18}$ Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, $C_{10}$–$C_{18}$ Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated $C_{12}$–$C_{18}$ Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lanolin and Lanolin Derivatives, Lard, Lauric/Palmitic/Oleic Triglyceride, Lesquerella Oil, Linseed Oil, Macadamia Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, and the like, as well as mixtures thereof.

Fatty Acids: Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Fatty Alcohols: Behenyl Alcohol, $C_9$–$C_{11}$ Alcohols, $C_{12}$–$C_{13}$ Alcohols, $C_{12}$–$C_{15}$ Alcohols, $C_{12}$–$C_{16}$ Alcohols, $C_{14}$–$C_{15}$ Alcohols, Caprylic Alcohol, Cetearyl Alcohol, Cetyl Alcohol, Coconut Alcohol, Decyl Alcohol, Hydrogenated Tallow Alcohol, Lauryl Alcohol, Myristyl Alcohol, Oleyl Alcohol, Palm Alcohol, Palm Kernel Alcohol, Stearyl Alcohol, Tallow Alcohol, Tridecyl Alcohol, and the like, as well as mixtures thereof.

Essential Oils: Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

Sterols and/or Sterol Derivatives: As used herein, suitable sterols and sterol derivatives include, but are not limited to, the following materials: -sterols having a tail on the 17 position and having no polar groups for example cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, avocadin, sterol esters, and the like, as well as mixtures thereof.

Emollients: As used herein, suitable emollients include, but are not limited to, the following materials: Mineral Oil, Mineral Jelly, Petrolatum, cosmetic esters, fatty esters, glyceryl esters, alkoxylated carboxylic acids, alkoxylated alcohols, fatty alcohols, lanolin and lanolin derivatives, petrolatum base oils, silicones, fats, hydrogenated vegetable oils, polyhydroxy esters, and the like, as well as mixtures thereof.

Waxes: As used herein, suitable waxes include, but are not limited to, the following materials: natural and synthetic waxes, such as bayberry wax, beeswax, $C_{30}$ alkyl dimethicone, candelilla wax, carnuaba, ceresin, cetyl esters, hydrogenated cottonseed oil, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, motan acid wax, motan wax, ouricury wax, ozokerite, paraffin, PEG-6 beeswax, PEG-8 beeswax, rice bran wax, shellac wax, spent grain wax, steryl dimethicone synthetic beeswax, synthetic candelilla wax, synthetic carnuba wax, synthetic japan wax. Synthetic jojoba wax, synthetic wax, and the like, as well as mixtures thereof. The preferred waxes include but are not limited to; carnuba, cerasin, cetyl esters, microcrystalline wax, montan wax, ozokerite, synthetic wax, and the like, as well as mixtures thereof.

Humectants may also be included in the composition to provide an enhanced barrier and/or skin moisturization benefit. Humectants are typically cosmetic ingredients used to increase the water content of the top layers of the skin. This group of materials includes primarily hydroscopic ingredients. As used herein, suitable humectants include, but are not limited to, the following materials Acetamide MEA, Aloe Vera Gel, Arginine PCA, Chitosan PCA, Copper PCA, Corn Glycerides, Dimethyl Imidazolidinone, Fructose, Glucamine, Glucose, Glucose Glutamate, Glucuronic Acid, Glutamic Acid, Glycereth-7, Glycereth-12, Glycereth-20, Glycereth-26, Glycerin, Honey, Hydrogenated Honey, Hydrogenated Starch Hydrolysate, Hydrolyzed Corn Starch, Lactamide MEA, Lactic Acid, Lactose Lysine PCA, Mannitol, Methyl Gluceth-10, Methyl Gluceth-20, PCA, PEG-2 Lactamide, PEG-10 Propylene Glycol, Polyamino Sugar Condensate, Potassium PCA, Propylene Glycol, Propylene Glycol Citrate, Saccharide Hydrolysate, Saccharide Isomerate, Sodium Aspartate, Sodium Lactate, Sodium PCA, Sorbitol, TEA-Lactate, TEA-PCA, Urea, Xylitol, and the like, as well as mixtures thereof.

The composition may also include emulsifying surfactants. The surfactants include, but are not limited to, sorbitan monooleate, sorbitan sesquioleate, sorbitan trioleate, glyceryl stearate, sorbitan stearate, sorbitan tristearate, and the like, as well as mixtures thereof.

The composition may also include viscosity enhancers. As used herein, suitable viscosity enhancers include, but are not limited to, the following materials: the group consisting of polyolefin resins, polyolefin polymers, ethylene/vinyl acetate copolymers, polyethylene, and the like, as well as mixtures thereof Ingredients of lipophilic sequestering agent compositions can also include, but are not limited to, humectants, surfactants, and viscosity enhancers present in an amount ranging from about 0.1% to about 10.0% of the total weight of the lipophilic sequestering agent composition.

It will be apparent to those skilled in the art that additional agents may be desirable for inclusion in the present composition. Examples include, but are not limited to, acceptable carriers, anti-inflammatories, antimicrobials, antipuretics, skin protectants, buffering agents, -hydroxy acids, microbial or algal extracts and/or fractions thereof, enzyme inhibitors, antihistamines, antioxidants, analgesics, antioxidants, astringents, fragrances, dyes, natural and/or synthetic vitamin analogs, sunscreens, deodorants, and combinations thereof.

Therefore, the present invention provides that both hydrophilic and hydrophobic inflammatory agents in nasal secretions can be sequestered onto the stratum corneum with a combination of both modified and non-modified sequestrant particles. The sequestering agents can be delivered to the stratum corneum either directly from the substrate, or by an acceptable vehicle. Sequestrants can be delivered with a facial tissue either alone or when contained in one or more of the aforementioned vehicles.

In certain embodiments, it is desirable, but not necessary, that the sequestering agent particles do not detract from the tactile attributes of the finished product. The invention provides in some embodiments an upper limit of 25 $\mu$M, and more desirably less than 15 $\mu$M for the sequestering agent particle diameter. In one embodiment, the sequestering agents comprise about 0.001% to about 5.0% of the total weight of the sequestering agent/substrate combination. In another embodiment, the sequestering agents comprise about 0.01% to about 1.0% of the total weight of the sequestering agent/substrate combination.

As stated above, in one embodiment, the sequestering agent for the present invention is a combination of non-modified and modified bentonite clay. As used herein, "unmodified" or "non-modified" describes clay or other suitable sequestrant material that has not been significantly chemically modified other than to process and/or purify the native material. Synthetic clays that have not been modified to be organophilic are also considered as unmodified or non-modified for the purposes of this invention. In its natural state, clay is hydrophilic, and therefore, charged. As used herein, "organophilic" describes modified clay or other suitable material where the naturally occurring charge has been significantly reduced by adding relatively hydrophobic material to the surface of the native material. For instance, modifications to clays have been accomplished using a variety of techniques including derivatization with phenolic, quaternary ammonium, methyl methacrylate compounds. Likewise, "modified" sequestering agents are made by adding any number of specific compositions to the surface of a non-modified sequestrant to impart enhanced affinity for target irritant(s). A few illustrative examples include, but are not limited to, particulate matter coated with antibodies, lectins, or hydroxyapatite. A variety of hydrophobic particle modifications will be obvious to the artisan that is consistent with the invention described herein.

The ability to sequester relatively hydrophobic irritants may be accomplished by modifying native materials by a variety methods known to impart hydrophobic surface properties to native materials. The resulting organophilic materials and the methods for producing them are well known to those skilled in the art[26,27]. For instance modifications to clays have been accomplished using a variety of techniques including derivatization with phenolic, quaternary ammonium, methyl methacrylate compounds[28,29,30]. Likewise, methods to modify the surfaces of silica have been published as well[31,32,33,34]. Additionally, hydroxyapatites have been modified using similar techniques[35,36]. Titanium dioxide has also been derivatized with quaternary ammonium surfactants to increase the ability of hydrophobic molecules to interact with the resulting material[37]. These modifications are all suitable for hydrophobic sequestering agents of the present invention.

It is clear that different irritants may be optimally bound by differing sequestrants. Therefore, the invention includes the use of one or more sequestrants for the contemporaneous binding of multiple irritants. Singular sequestrants such as modified and organophilic materials can be used alone for sequestering skin irritants present in nasal secretions. Additionally, the substrate may include any permutations of mixes of different native (non-modified) sequestrants, organophilic sequestrants, and modified sequestrants. Indeed, mixes of sequestrants, all of which are from a singular class, all modified or all organophilic, could also have utility for binding target irritants present in nasal secretions.

In some instances, it may be desirable to provide spatial separation of one or more of the different sequestrants to preclude undesirable interactions between said sequestrants. This can be accomplished by a variety of means. For example, one sequestrant could be included in a tissue or other non-woven sheet while another was applied on the surface. Patterned printing of two or more sequestrants would achieve spatial separation as well. Alternately, a multi-plied product with sequestrants present in different surfaces or plies or embedded between surfaces or plies could again provide for spatial separation of the sequestrants. Further it is possible to achieve spatial separation of different sequestrants by placing them in different layers of a given ply and/or different plies. Fibers used to prepare the sheet could also be selected and/or modified to provide irritant sequestration attributes. Different fibers could bear different sequestrants and thereby, again, provide for spatial separation of sequestrants. It is possible to use various permutations of the above approaches to achieve spatial separation of different sequestrants.

Heterogeneous spatial distribution of sequestrants may also be desirable to provide for greater economy of sequestrant use. For instance, sequestrants might be applied only to outer plies of a three-ply product or only to the center of the tissue surface. Other spatial distribution patterns for achieving economic use of sequestrants will be obvious to those skilled in the art.

The invention also provides for one or more sequestrants to be relatively substantive to the tissue or other non-woven or woven material while one or more particulate sequestrants are transferred to the skin. Such an embodiment would provide for both irritant binding to the product as well as irritant binding to sequestrants deposited on the skin surface.

Figure 5:
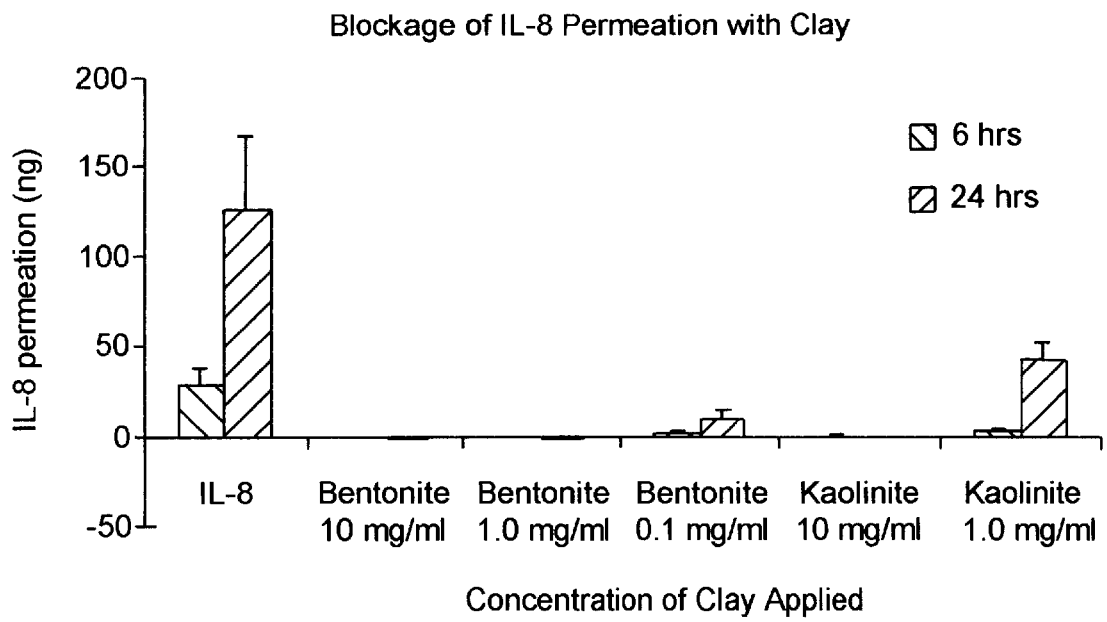
FIG. 5 shows that clay pretreatment retards the penetration of the skin irritant IL-8 through an in vitro skin model.
Figure 6:
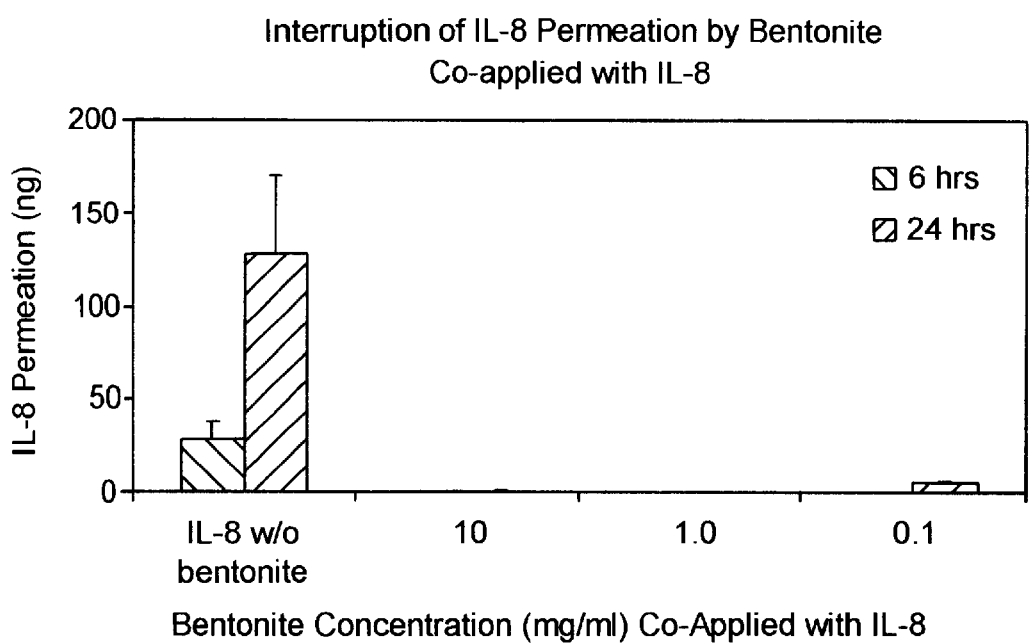
FIG. 6 shows that clays co-applied with the skin irritant IL-8 can retard the penetration of IL-8 through an in vitro skin.

It is difficult to quantify the actual amount of modified and/or non-modified sequestering agent(s) that must be applied to the skin. Different sequestrants will have disparate capacities for binding various irritants and, accordingly, more or less will be required depending on the choice of sequestrant(s) used. However, it is critical that enough is used to produce a substantial decrease in the irritation caused by nasal secretions. When the sequestering agent is clay, typically, the amount of modified and non-modified clay applied to the skin will be in the range of about 0.01 $\mu$g per square centimeter to about 100 $\mu$g per square centimeter. The results of FIGS. 5 and 6 show that at a dose equivalent to about 4.0 $\mu$g sequestrant/cm$^2$ skin of bentonite was highly effective.

The clay used in the invention is typically applied to the skin in a dermatological composition comprising a suspension of the organophilic and non-modified clay in an acceptable vehicle. Suitable vehicles include organic and aqueous liquids, anhydrous formulations, lotions, creams, emulsions, gels or the like. The organophilic and non-modified clay can also be applied in finely divided form as a mixture with a dusting powder, e.g., as a mixture with a talcum powder or a finely divided starch powder. Modified clays may also be used in the above substrate configurations.

The topically applied protective composition (vehicle containing sequestrants) may also act as a barrier to prevent irritants from coming into contact with the skin. The vehicle may contain emollients to aid in healing irritated skin and dispersants to keep the clays in suspension. The vehicle should preferably be inert with respect to the clays, i.e., it should be devoid of materials that would themselves adsorb to the clays and thereby diminish the adsorptive capacity of the clay to the point where the sequestrants are no longer effective.

The non-modified, organophilic and modified sequestrants that comprise the sequestering agents of the present invention may be any conventional sequestrant of commerce suitable for cosmetic use. By way of example, clays are well known and can be utilized as sequestrants in the present invention. They can be prepared from any of the clays of the smectite class that are known to swell in water and/or hydrophilic solvents to form viscous suspensions. Suitable clays include naturally occurring montmorillonite, bentonite, beidellite, hectorite, saponite and stevensite, and their synthetically made counterparts such as Laponite for example. These clays have a lamellar structure wherein alkali metal ions are distributed between the lamellae. The hydrophilic clays occur naturally. Treatment of these clays with long-chain compounds that contain substantial hydrophobic regions (for example, long-chain quaternary amines) imparts increased hydrophobicity to the clay and thereby renders the clay organophilic.

The quaternary ammonium compounds used in preparing the organophilic modified clay component of the skin-protecting composition used in the method of the invention typically have one or two long-chain substituents, e.g., 14–20 carbon atoms, and two or three short-chain substituents such as methyl groups. A preferred quaternary ammonium compound is dimethyl dihydrogenated tallow ammonium chloride. Because the tallow contains a large proportion of stearic acid, which contains 18 carbon atoms, the resulting clay is often referred to as a quaternium 18 clay, e.g., quaternium 18 bentonite, or quaternium 18 hectorite. The composition and preparation of such organophilic clays is well-known. In one embodiment, the modified organophilic clay for use in this invention is quaternium 18 bentonite.

It will be apparent to those skilled in the art that additional agents may be desirable for inclusion in the present composition. Examples include, but are not limited to, acceptable vehicles, anti-inflammatories, antimicrobials, antipruretics, skin protectants, lipids, buffering agents, hydroxy acids, microbial or algal extracts and/or fractions thereof, enzyme inhibitors, moisturizers, antihistamines, antioxidants, analgesics, antioxidants, fragrances, dyes, natural and/or synthetic vitamin analogs or mixtures thereof.

The inclusion of these agents with sequestrants will afford benefits relative to similar compositions devoid of sequestrants. Any irritants that do achieve access to the viable layers of nasolabial skin will be less likely to have a deleterious effect on skin health due to the inclusion of a(n) additional agent(s) as referenced above. Said agents will have an increased likelihood of counteracting the irritants as the quantity of irritant achieving access to the skin is reduced by the sequestrants.

It has now been found that a particularly suitable sequestering agent is clay, in particular bentonite clay. Bentonite clay is known by one of ordinary skill in the art to be a readily available, natural occurring clay. One embodiment of the present invention entails a combination of both organophilic and non-modified bentonite clay being present on the paper facial tissue.

In one embodiment, both hydrophilic and hydrophobic sequestering agents are carried by a paper fiber tissue for delivery to the skin. The process of making paper fiber tissue are known to the skilled artisan and are outlined in U.S. Pat. No 5,672,248 for example, incorporated herein by reference.

Apart from specific hydrophobic and hydrophilic sequestering agents, the invention provides that the tissue paper substrate may further comprise fillers. Particulate fillers can be selected from clay, calcium carbonate, titanium dioxide, talc, aluminum silicate, calcium silicate, alumina trihydrate, activated carbon, pearl starch, calcium sulfate, glass microspheres, diatomaceous earth, and mixtures thereof.

Usually, these particulate fillers are applied in the wet end of the papermaking process by flocculating the filler with a cationic starch and using a cationic retention aid at the outlet of the fan pump. Flocculant size is often an important aspect of maintaining desirable opacity levels and strength in tissue products. If the flocculent particles are too large, good retention is achieved but with a significant loss of strength and poor opacity due to the reduction of air-filler and fiber-filler interfaces. On the other hand, if the flocculent particles are too small, retention is poor even though less strength is lost and greater opacifying efficiency is obtained.

Other additives include retention aids, a term as used herein, referring to additives used to increase the retention of the sequestering agents in the web during the papermaking process. Various anionic and cationic retention aids are known in the art. Generally, the most common anionic retention aids are charged polyacrylates, whereas the most common cationic retention aids are charged polyacrylamides. These retention aids agglomerate the suspended particles through the use of a bridging mechanism. A wide range of molecular weights and charge densities are available. In general, high molecular weight materials with a medium charge density are preferred for flocculating particulate fillers. The filler retention aid flocs are easily broken down by shear forces and are usually added after the fan pump.

Cationic starches are commonly used to agglomerate the clay or other filler particles. It is believed that the cationic starch becomes insoluble after binding to the anionically-charged filler particles. The goal of agglomeration is having the filler covered with the bushy starch molecules. The starch molecules provide a cationic surface for the attachment of more filler particles, causing an increase in agglomerate size.

The size of the starch filler agglomerates is an important factor in obtaining the optimal balance of strength and optical properties. Agglomerate size is controlled by the rate of shear supplied during the mixing of the starch with the filler. The agglomerates, once formed, are not overly shear sensitive, but they can be broken down over an extended period of time or in presence of very high shear forces.

The charge characteristic of the starch is significant as well. Since starch is usually employed at an amount of less than 5% by weight of filler, the filler-starch agglomerates possess a negative charge. In this case, a cationic retention aid is utilized.

Higher levels of starch are sometimes employed. In these instances, the filler-starch agglomerates may actually possess a net positive charge and would, thus, require the use of an anionic retention aid.

Nonparticulate fillers may also be employed. One such class of nonparticulate fillers includes thermoplastic microspheres. Such non-particulate fillers are generally applied as a coating in a post-treatment operation; however, they may be applied in the wet end.

Other materials can be added to the aqueous papermaking furnish or the embryonic web to impart other characteristics to the product or improve the papermaking process so long as they do not significantly and adversely affect the sequestering agents' biding affinity for the skin irritants.

Those skilled in the art will recognize that not only the qualitative chemical composition of the papermaking furnish is important to the papermaking process, but also the relative amounts of each component, and the sequence and timing of addition, among other factors.

EXAMPLES

Example #1

Nasal Secretions Elicit a Pro-inflammatory Response in a Human Skin Model

The EpiDerm™ skin model (MatTek Co.; Ashland, Mass.; Cat. #EPI-200-HCF) was employed to determine the pro-inflammatory (PI) properties of nasal secretions (NS). This objective was accomplished by adding pooled NS to the EpiDerm™ model and quantifying the induction of marker compounds indicative of cutaneous inflammation. These markers included a primary cytokine (IL-1α) and a secondary cytokine (IL-8) produced by the keratinocytes present in the EpiDerm™ model.

Nasal secretions were obtained from multiple individuals, stored at −70° C. until pooled. Upon thawing the NS were maintained at 4° until applied to the EpiDerm model. The NS samples were pooled into 50 ml polystyrene centrifuge tubes. Once pooled, the nasal secretions were centrifuged at 13 K×g for 5 minutes. The supernate was removed to a new 50 ml polystyrene centrifuge tube. The pellet was sonicated with a Virtis Virsonic Model #475 sonicator equipped with a CV4 Ultrasonic Converter for 1 minute. The resulting fluid was centrifuged as before and the supernatant added to the previous supernatant. Aliquots of the pooled supernates were stored at −70° C. until needed.

The EpiDerm™ model was handled as prescribed by the vendor. The EpiDerm™ surface was treated with 25 μl of pooled NS and returned to a 37° C. incubator with an atmosphere containing 5% $CO_2$ for 24 hours. These experiments were performed with n values of 6 for each treatment (one treatment per 6 well plate). Positive and negative controls were included with each experiment. The negative control was 25 μl of PBS while the positive control, 25 μl of phorbol-12-myristate-13-acetate (TPA) at 1 mg/ml. At the conclusion of the incubation period, the conditioned media was stored in a −70° C. freezer for future analysis.

The concentration of Interleukin-1α (IL-1α) and Interleukin-8 (IL-8) present in the conditioned media was determined using ELISA kits obtained from R&D Systems, Inc.; Minneapolis, Minn. (Cat. #DLA50 and #D8050 respectively). Differences in mean values between treatments were determined using the Student's t-test. The significance level was set at $P<0.05$.

Figure 2:
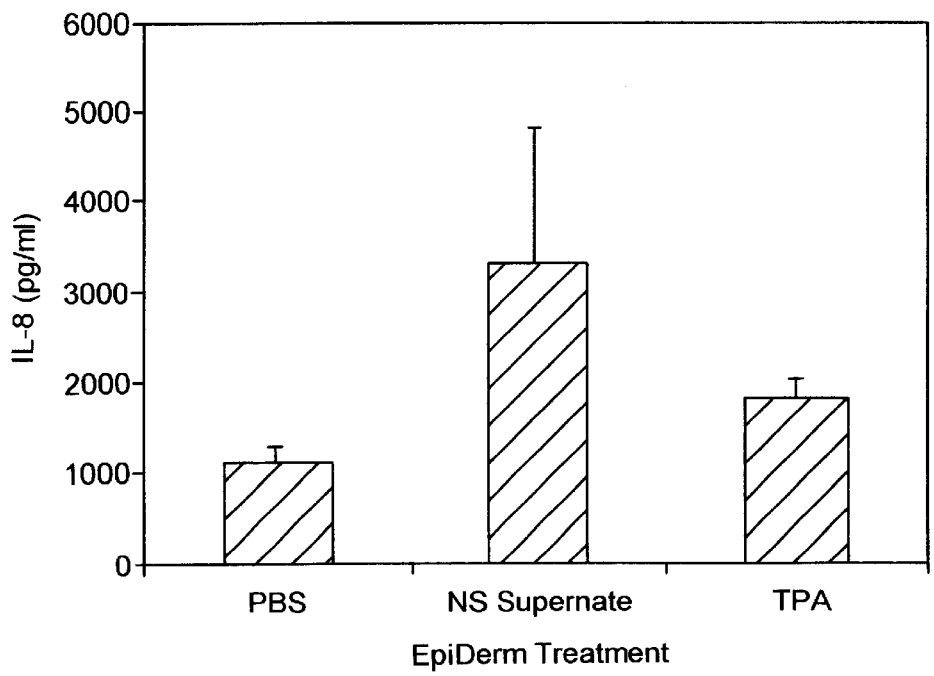
FIG. 2 shows a pro-inflammatory response (accumulation of IL-8) occurs when nasal secretions are applied to a living human skin model.

FIG. 1 demonstrates that significantly more IL-α is detected in the conditioned media underlying EpiDerm samples treated with NS relative to the negative control. FIG. 2 illustrates the same finding for IL-8. These results indicate that NS has pro-inflammatory properties when applied to a living human skin model.

Example #2

Suitability of Different Clays as Sequestrants for a Skin Irritant Present in Nasal Secretion Non-modified clays suspensions (10 mg/ml) were prepared in Eppendorf tubes. The fluid used to suspend the clays was achieve 50 mM phosphate buffer at pH 7.4 with 150 mM NaCl, 50 ng/ml IL-8, and 0.1% bovine serum albumin (BSA). Each clay suspension, bentonite (Sigma Cat. No. B-3378), kaolinite (Sigma Cat. No. K-7375), zeolite (Sigma Cat. No. Z-3125), and laponite clay (LAP RD MICRO Sample #12566–62028; Southern Clay Products, Inc.) was prepared in a separate Eppendorf tube. A control tube was prepared that contained the IL-8 solution without clay.

The resulting tubes were incubated for two hours on a rocking platform at room temperature. Then, the tubes were centrifuged at 10,000 rpm in an Eppendorf 5415C microcentrifuge for 10 minutes, and the supernatants transferred to fresh Eppendorf tubes and frozen at −70° C. for further analysis.

Figure 3:
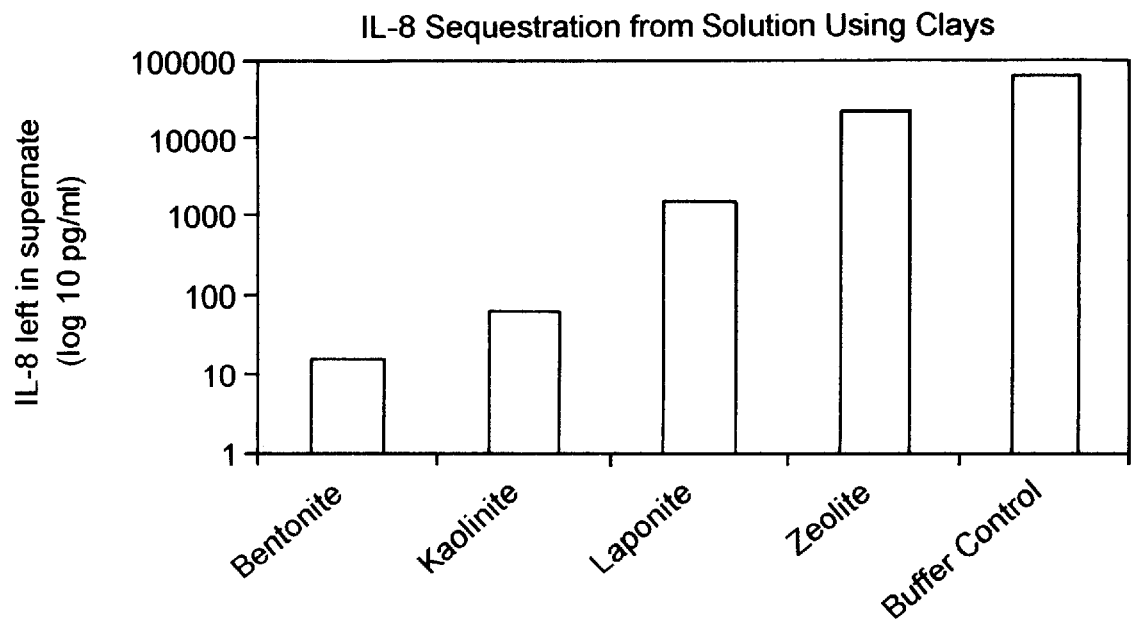
FIG. 3 shows the ability of various non-modified clays to sequester the skin irritant IL-8.

Samples were thawed and the IL-8 content was determined with the use of an R&D Systems IL-8 ELISA kit (Cat. #D8050). The amount of IL-8 present in the supernatant was compared to that recovered in the buffer control. Differences, representing loss of IL-8, were then measured as indices of sequestration activity. FIG. 3 shows the ability of various clays to sequester IL-8 from solution. The results indicate that the various clays have differing affinities for IL-8. The clay with the highest affinity for IL-8 was bentonite, followed by kaolinite, laponite and zeolite.

Example #3

Clay Sequestrants Prevent IL-8 Permeation Through a Human Skin Model

A skin model, MatTek's (Ashland, Mass.) EpiDerm™ skin model, (Cat. #EPI-200-HCF) was used in this experiment. The clays used were bentonite (Sigma Cat. No. B-3378) and kaolin (Sigma K-7375).

Four 10 ug vials of IL-8 (Sigma I-1645) were rehydrated with 250 µl distilled water each to provide about 1.00 ml of 40 µg/ml rhIL-8.

Clay suspensions were prepared by adding phosphate buffer to pre-weighed amounts of clay to achieve 20 mg/ml suspensions of both bentonite and kaolin. 2.0 and 0.2 mg/ml suspensions of both clays were prepared by serial 10-fold dilutions of the original clay suspensions.

Both the interleukin-8 (IL-8) and clay suspensions were prepared at 2.0× their final concentrations. For a co-deposition procedure, 100 µl IL-8 stock (2×) and 100 µl of clay suspension (2×) were mixed in a 1.5 ml Eppendorf tube. 25 µl aliquots were added to the Eppendorf model. For an ordered deposition procedure, 12.5 µl of the 2.0× clay suspension was applied to the EpiDerm model followed by 12.5 µl of the 2.0× IL-8 solution. In the control, 100 µl of IL-8 solution and 100 µl of phosphate buffer were added to a 1.5 ml Eppendorf tube, mixed and 25 µl added to the EpiDerm model.

The EpiDerm was pre-incubated and incubated according to the manufacturer's instructions, except in 1.0 ml of assay medium rather than 0.9 ml. Treatments were applied to the surface of the EpiDerm skin model as described above. Fifty µl of the media was sampled at 6 hours, and the remainder collected at 24 hours. Tubes were immediately placed on crushed ice following collection, and once all samples were collected, they were immediately transferred to a −70° C. freezer until analyzed.

The IL-8 content of the media was determined using R&D Systems IL-8 ELISA kit (Lot No. D-8050) after thawing and diluting the samples.

Figure 4:
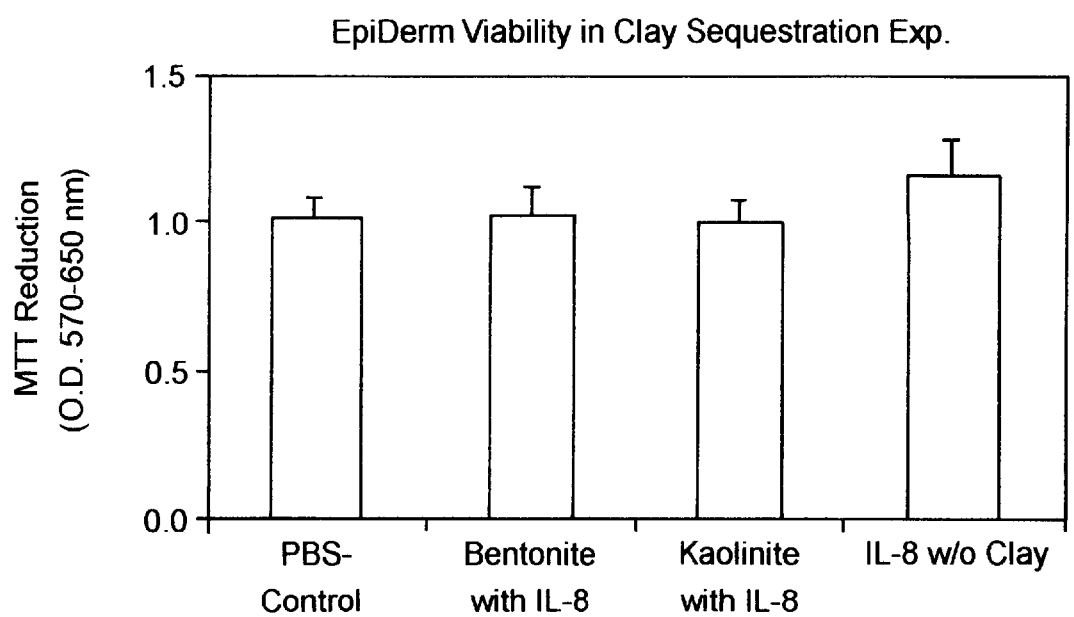
FIG. 4 shows that clays applied to a skin model do not elicit cytotoxic events as measured by an MTT assay.

Cellular viability of the EpiDerm was determined using the vendor-supplied MTT kit (3-[4,5-dimethylthiazol-2-yl]-2,5-diphenyltetrazolium bromide). The viability results, shown in FIG. 4, indicate that the clays do not adversely effect cell viability. The blockage of IL-8 permeation by pretreatment with clays is shown in FIG. 5. The blockage of IL-8 permeation with co-applied clays is shown in FIG. 6. Both bentonite and kaolinite inhibit the permeation of the skin irritant IL-8 present in nasal secretions. Bentonite appears to have a greater effect than kaolinite in the Epi-Derm model.

Example #4

Kinetics of Interleukin-8 Binding to Bentonite

The determination of how fast interleukin-8 (IL-8) binds to bentonite is important for elucidating practical methods of sequestering on the skin. Therefore, 50 mM phosphate buffer with 150 mM NaCl and 0.1% bovine serum albumin (BSA) was prepared. A double strength suspension of non-modified bentonite was prepared in the above buffer at a concentration of 20 mg/ml. Likewise, a solution of IL-8 was prepared at a concentration of 500 mg/ml by rehydrating a 10 ug vial of IL-8 (Sigma Cat. No. I-1645, Lot No. 117H0247) with 500 μl of distilled water. 125 μl was transferred to 4.9 ml of phosphate buffer to arrive at a concentration of 500 ng/ml.

500 μl of the 2× clay suspension was added to an Eppendorf tube along with 500 μl of the IL-8. The control tube contained 500 μl phosphate buffer along with 500 μl of IL-8 solution (no clay). The tubes were placed on a tube rocker at room temperature for 1, 2 and 8 minutes (the control tube was placed on the rocker for 8 minutes). Immediately after the incubation period, the tubes were placed in an Eppendorf 5415C microcentrifuge (10,000 rpm for 5 minutes at room temperature) to pellet the clay. The supernatant was removed and transferred to fresh 1.5 ml Eppendorf tubes. The amount of IL-8 remaining in the supernatant was determined.

The clay supernatants contained the amounts of IL-8 at the time points as shown in Table #1. These results demonstrate that the binding of IL-8 to clay is extremely rapid and thorough.

TABLE #1

| Timepoint (minutes) | IL-8 Remaining (pg/ml) | IL-8 Removed (% of Control) |
|---|---|---|
| Control | 373,000 | Not applicable |
| 1 | 1,063 | 99.71 |
| 2 | 792 | 99.78 |
| 8 | 755 | 99.80 |

Example #5

Contemporaneous Sequestration of Multiple Skin Irritants to Non-modified Bentonite Previous studies have shown that bentonite can remove skin irritants from solution using IL-8 as a model skin irritant relevant to nasal secretions. This experiment expands the scope of this investigation by including other putative skin irritants present in nasal secretions, including IL-1α, IL-1β, IL-8 and $PGE_2$. Activities of each sequestrant with each irritant present alone and in combination were evaluated.

Target concentrations of each irritant were chosen to reflect the upper end of concentrations that are observed in nasal secretions. The irritants used were $PGE_2$ (Calbiochem Catalogue No. 538904, Lot No. B21932), IL-1 alpha (R&D Systems 200-LA, Lot #AC147071), IL-1 beta (Sigma I-4019, Lot #10640049) and IL-8 (Sigma I-1645, Lot #11740247). The sequestrant utilized was bentonite (Sigma B-3378, Lot #67H1576). Suspensions of bentonite were prepared at two concentrations (11.11 mg/ml and 16.67 mg/ml as 1.1× and 1.66× of working strength, respectively).

Solutions of the skin irritants were prepared at 10× target concentrations. In this way, the addition of part irritant stock (at 10× working strength) to 9 parts of clay suspension (at 1.1× working strength) would result in a suspension where both clay and irritant concentrations were 1×. The diluent used for the clay suspensions and irritant dilutions was 50 mM TRIS buffer at pH 7.5 with 150 mM NaCl and 1% BSA.

The sequestration of singular irritants was performed by adding 100 μl of 10× irritant stock solution to 900 μl of 1.11× bentonite suspension in a 1.5 μl Eppendorf tube. The tubes were placed in a rocker for 1 hour at room temperature. Tubes were centrifuged at 10,000 rpm for 10 minutes (Eppendorf Microcentrifuge 5415C). 500 μl of each supernatant was removed and transferred to a fresh tube for freezing at −70° C. until later analysis.

Contemporaneous sequestration of all four irritants was accomplished in a similar fashion except that 100 μl of each stock solution was added to 600 μl of 1.667× bentonite solution.

Bentonite supernate was prepared using diluent buffer to suspend the bentonite at 10 mg/ml, centrifuging the suspension after an incubation period similar to that described for the test suspensions. However, this was done on a larger scale using 50 ml tubes. The tubes were centrifuged for 5 minutes in a J-251 Beckman ultra-centrifuge equipped with a J-12 rotor at 9,000 rpm. The resulting supernatant was filtered through a 5 μm sterile Acrodisc (Gelman Cat. #4199) equipped with a low protein-binding filter (Gelman Sciences; Ann Arbor, Mich.). 900 μl aliquots were placed in 1.5 ml Eppendorf tubes along with 100 μl of irritant stock solution (10×). This was done in parallel for each irritant to ensure that components of the clay suspension supernatants did not interfere with the subsequent ELISA (comparison of "buffer alone" to "supernate alone").

ELISA kits for each irritant ($PGE_2$, IL-1α, IL-1β, and IL-8) were obtained from R&D Systems (Minneapolis, Minn.) and used to quantify the analytes present in the samples.

Figure 7:
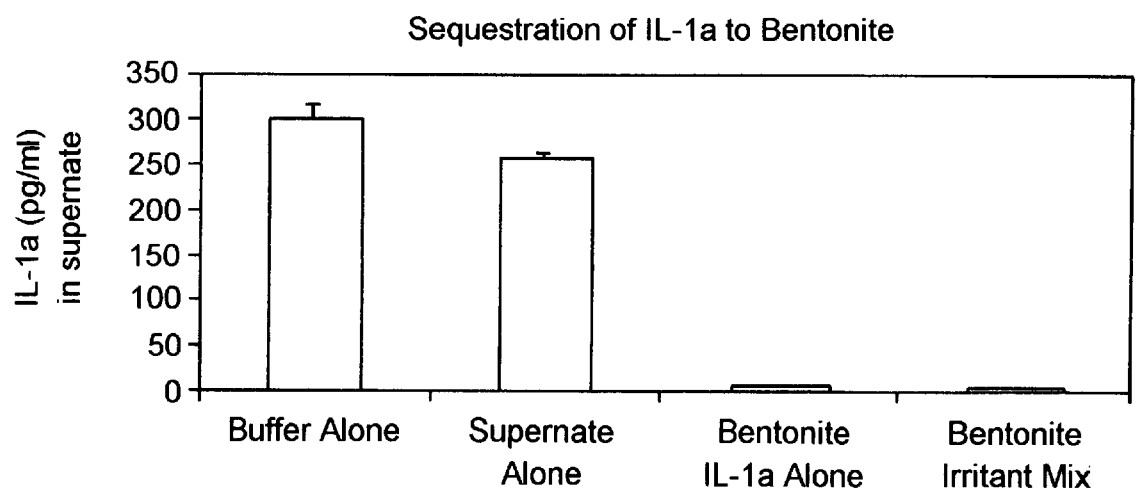
FIG. 7 shows the ability of non-modified bentonite clay to bind the skin irritant interleukin-1α when present either alone or in combination with other skin irritants.
Figure 8:
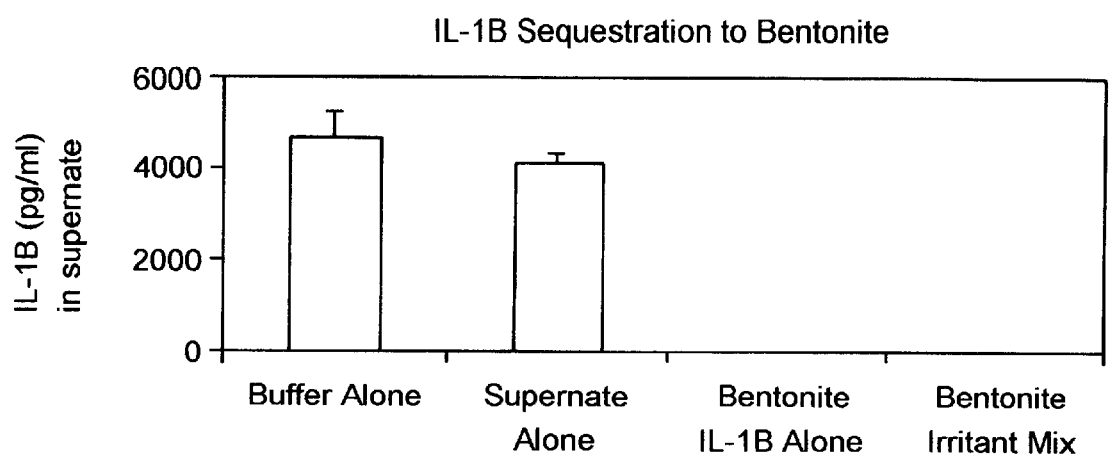
FIG. 8 shows the ability of non-modified bentonite clay to bind the skin irritant interleukin-1β when present either alone or in combination with other skin irritants.
Figure 9:
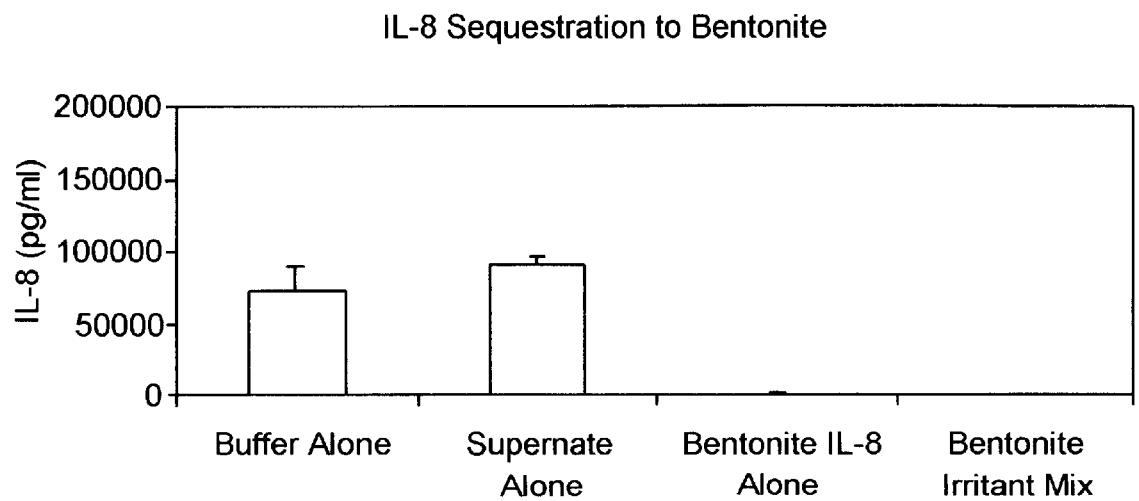
FIG. 9 shows the ability of non-modified bentonite clay to bind the skin irritant IL-8 when present either alone or in combination with other skin irritants.
Figure 10:
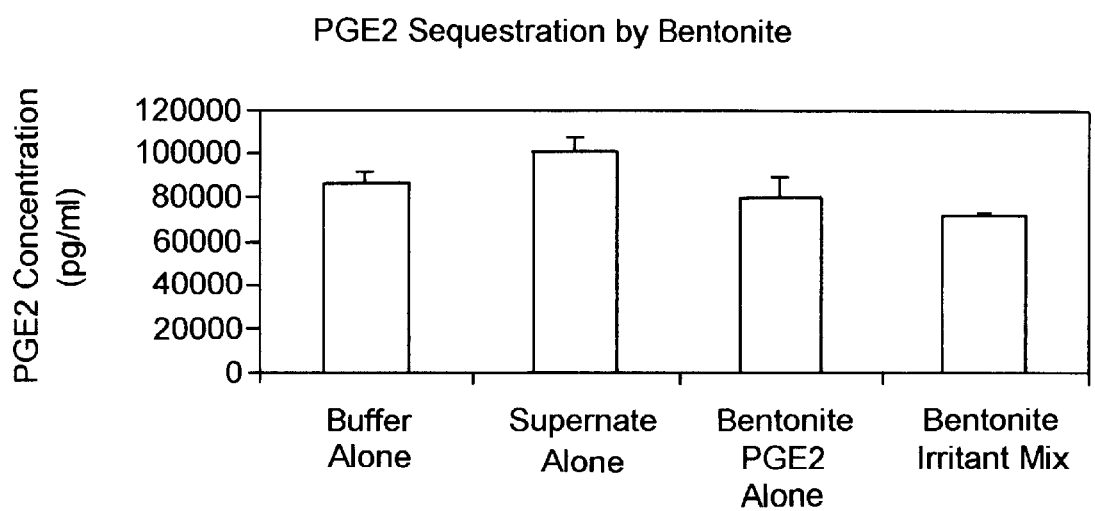
FIG. 10 shows the ability of non-modified bentonite clay to bind the skin irritant $PGE_2$ when present either alone or in combination with other skin irritants.

FIG. 7 shows the results of IL-1 alpha sequestration by bentonite. FIG. 8 shows the results of IL-1 beta sequestration by bentonite. FIG. 9 shows the results of IL-8 sequestration by bentonite. FIG. 8 shows the results of $PGE_2$ sequestration by bentonite.

All cytokines were effectively removed from solution by the clay. This was true if added singularly or in combination to the clay suspensions. The fraction of $PGE_2$ removed from solution solutions by the non-modified bentonite was not nearly as large as that realized for the cytokines. This may be due to the relative hydrophobicity and/or the chemical composition of $PGE_2$.

Example #6

Sequestration of Skin Irritants from Buffer and Nasal Secretions Using Non-Modified and Organophilic Clays This experiment seeks to evaluate the ability of various materials to remove (sequester) irritants from both solution and human nasal secretions.

Sequestration buffer (50 mM phosphate buffered at pH 7.4 with 150 mM NaCl and 0.1% bovine serum albumin (BSA)) was prepared. A 1.11× solution of IL-8 (Sigma Cat. No. I-1645, Lot No. 117H0247) was prepared at a concentration of 555 ng/ml in sequestration buffer.

For determining IL-8 sequestration in buffer, nine parts of 1.11× IL-8 in sequestration buffer was added to 1 part of a 10× clay suspension. Specifically, 630 μl of IL-8 (@ 555ng/ml) in sequestration buffer was placed in a 1.5 ml Eppendorf tube along with 70 μl of 10× non-modified bentonite suspension (100 mg/ml). Similarly, tests were also performed with an organophilic montmorillonite clay modified by quarternary ammonium, available as Claytone APA (Southern Clay Products, Gonzales, Tex.) using the same approach described above for non-modified bentonite. In both cases the sequestrant IL-8 mixes were incubated on a rocker platform at room temperature for 30 minutes, and centrifuged for 10 minutes at 10,000 rpm in an Eppendorf microcentrifuge. The supernatant was collected, and frozen at −70° C. until analyzed. Sequestration was determined by comparing the amount of IL-8 remaining in the supernate to that of IL-8 added to a similar tube devoid of clay.

Nasal secretions previously collected in an undiluted form from an individual were stored at −70° C. They were thawed and centrifuged at 10,000 rpm at 4° C. in a Beckman J-251 ultracentrifuge equipped with a JA-12 rotor for 10 minutes. The supernatant was removed from each tube and pooled into a clean sterile 50 ml polystyrene centrifuge tube. The pellets were combined in a similar tube and sonicated for 15 seconds using a Virtis Virsonic 475 sonicator equipped with a CV4 converter. The sonicated material was centrifuged as before and the resulting supernatant was added to the previous supernatant. This procedure is necessary to permit handling of the viscous material.

For determining IL-8, $PGE_2$, and $LTB_4$ sequestration from nasal secretions the test was performed as described above for determining sequestration in a buffer background. However, the volumes were different in that 20 μl of a 10× clay suspension were added to 180 μl of nasal secretions. Sequestration was determined by comparing the amount of analyte (IL-8, $PGE_2$, and $LTB_4$) remaining in the nasal secretion supernate to that of the nasal secretion control. The control was prepared in a similar tube without clay (20 μl of sequestration buffer devoid of clay was added to 180 μl of nasal secretion).

Figure 11:
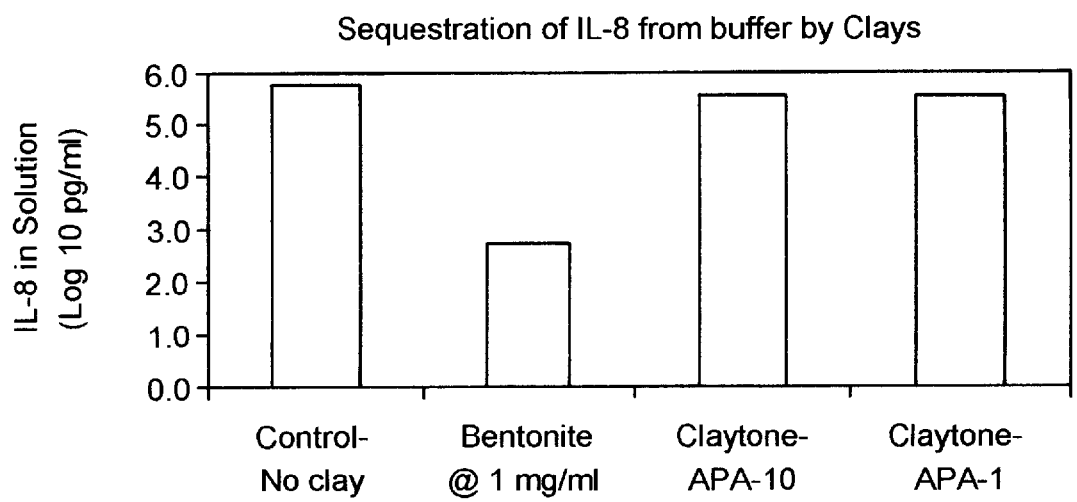
FIG. 11 shows the ability of both derivatized and non-modified clays to bind the skin irritant IL-8.

FIG. 11 illustrates the removal of the skin irritant IL-8 from buffer by non derivatized bentonite and Claytone APA. These results demonstrate that non-modified bentonite is superior for the removal of IL-8 from solution relative to the derivatized clay. The bentonite was found to remove 99.9% of the IL-8 from solution whereas the organophilic clay (montmorillonite modified with quaternary ammonium compounds) were far less effective, removing ~20% of the IL-8 from solution.

Figure 12:
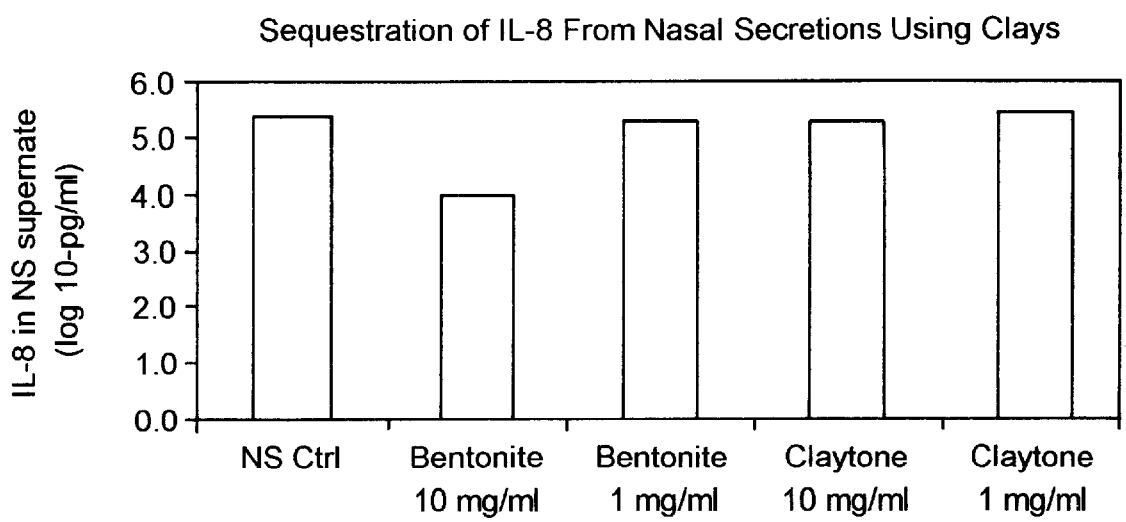
FIG. 12 shows the ability of both derivatized and non-modified clays to bind the skin irritant IL-8 from human nasal secretions.

FIG. 12 demonstrates that non-modified bentonite is able to remove 95% of the skin irritant IL-8 from human nasal secretions, whereas the organophilic clay has little activity, removing only ~10% of the IL-8.

FIG. 13 provides evidence to suggest that organophilic clay modified with quaternary ammonium compounds can remove more (81%) of the eicosanoid $PGE_2$ from human nasal secretions whereas non-modified bentonite has less activity (16% removal). Similarly, FIG. 14 demonstrates that the organophilic clay has a higher affinity for the eicosanoid $LTB_4$ relative to non-modified bentonite. The organophilic clays may have an increased affinity for the eicosanoids due to their relatively hydrophobic nature imparted by the quaternary ammonium compounds that decorate them. Consequently, the lipid-derived eicosanoids will have a higher affinity for modified clays. This makes the modified clays particularly well suited for binding these specific irritants from nasal secretions. The results of this experiment illustrate the utility of using two different sequestrants for the contemporaneous removal of two different skin irritants when present in nasal secretion.

Example #7

Sequestrants Retain Their Ability to Sequester Skin Irritants from Nasal Secretions when Present in a Prototypic Lotion Vehicles The ability of lotions to sequester IL-8 from solution was determined in an experiment similar to that described in Example #6 above.

For determining IL-8 sequestration in lotion, nine parts of 1.1× IL-8 in sequestration buffer was added to 1 part of test lotion (containing non-modified bentonite), control lotion (devoid of the bentonite), or a 10× non-modified bentonite suspension. Specifically, 630 μl of IL-8 (@ 555 ng/ml) in sequestration buffer was placed in a 1.5 ml Eppendorf tube along with 70 μl of a test lotion (1% non-modified bentonite), or control lotion, or 10 mg/ml non-modified bentonite suspension (100 mg/ml). The sequestrant IL-8 mixes were incubated on a rocker platform at room temperature for 30 minutes, and centrifuged for 10 minutes at 10,000 rpm in an Eppendorf microcentrifuge. The supernatant was collected, and frozen at −70° C. until analyzed. Sequestration was determined by comparing the amount of IL-8 remaining in the supernate to that of IL-8 added to a similar tube devoid of the lotion vehicle or clay.

Three emulsions (lotions A, B, and C) were prepared. Before emulsification, clay (bentonite, Sigma Cat #B-3378) was added to the water and glycerin (Lotion A) mixture, or to the Polawax and Formula 1 mixture (Lotion B). Once a homogeneous dispersion of clay was achieved in the water/glycerin mix or the Polawax/Formula 1 mix it was emulsified with the remainder of the formulation (devoid of clay) to achieve the final lotion. The control lotion (Lotion C) was prepared without clay.

| Components | Lotion A wt % | Lotion B wt % | Lotion C wt % |
| --- | --- | --- | --- |
| Water | 74 | 74 | 75 |
| Glycerin | 5 | 5 | 5 |
| Polawax[a] | 10 | 10 | 10 |
| Formula 1[b] | 10 | 10 | 10 |
| Bentonite | 1 | 1 | — |

[a]Polawax is available from Croda, LTD. (Parsippany, NJ.) and is referred to as Emulsifying Wax NF by the International Nomenclature Cosmetic Ingredient (INCI).
[b]Formula 1 contains Mineral oil (59.8%), Dimethicone (1.0%), Isopropyl palmitate (3.0%), Aloe extract (0.1%), Vitamin E acetate (0.1%), Cerasin (18%), and Stearyl alcohol (18%).

Figure 15:
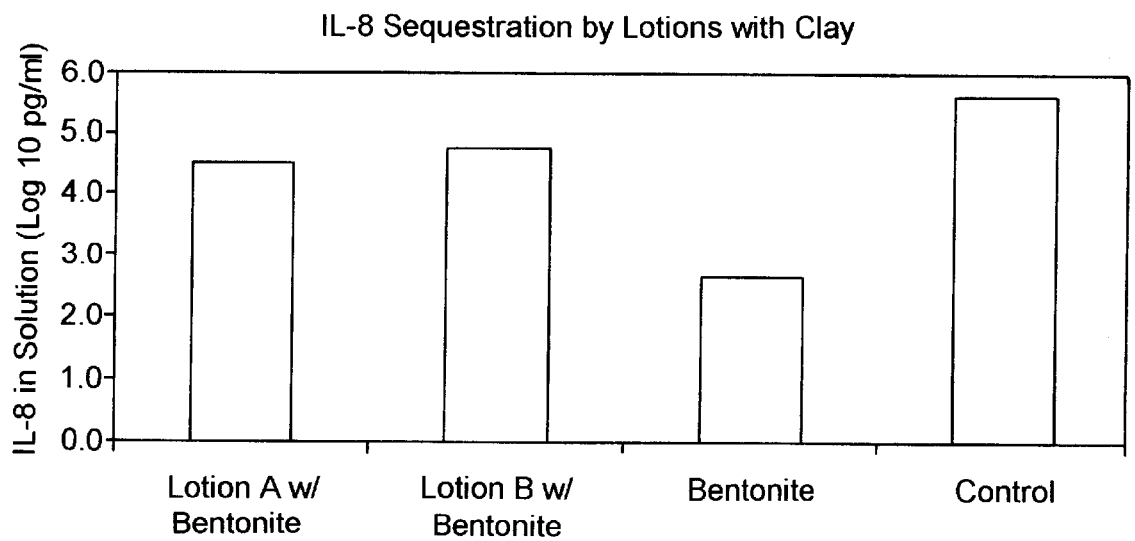
FIG. 15 shows the ability of non-modified bentonite to bind the skin irritant IL-8 when present in lotion vehicles.
Figure 16:
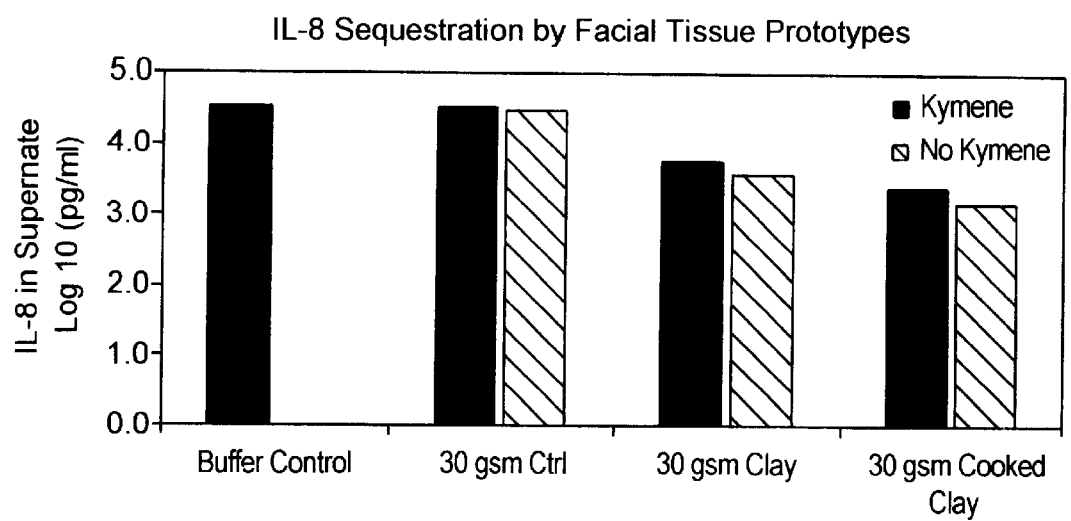
FIG. 16 shows the ability of facial tissues, with and without the inclusion of non-modified bentonite, to bind the skin irritant IL-8.
Figure 17:
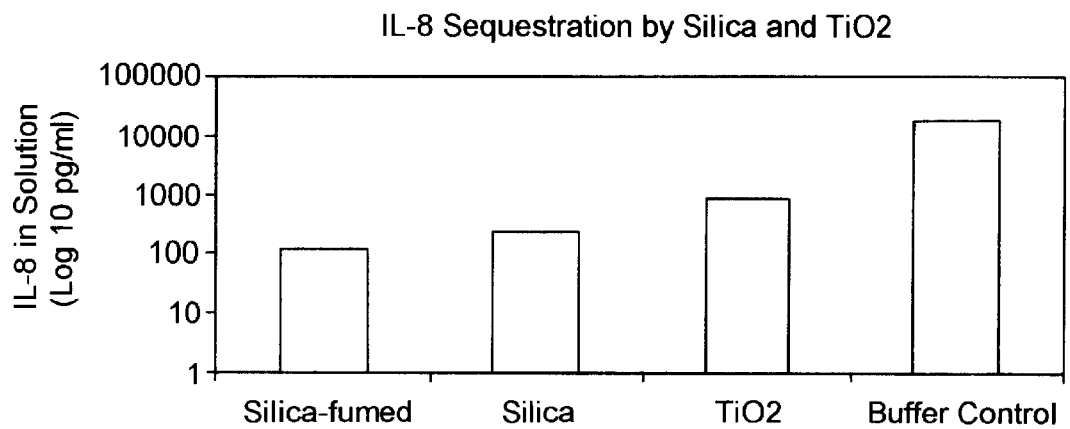
FIG. 17 shows the ability of non-modified silica and $TiO_2$ to bind the skin irritant IL-8.

FIG. 15 shows the results of IL-8 sequestration by lotions containing non-modified bentonite. This demonstrates that, as described above, non-modified bentonite is able to bind IL-8 and remove it from solution. Additionally, the inclusion of non-modified bentonite in the emulsion (1wt %) resulted in the removal of IL-8 from solution by about 90% whereas a lotion devoid of clay had no detectable affinity for the IL-8.

Example #8

The Inclusion of Clay to Facial Tissue Prototypes Provides for a Facial Tissue with an Affinity for the Skin Irritant IL-8

Tissue prototypes were prepared on a laboratory scale to attain 30 gsm handsheets with and without the addition of non-modified bentonite. In one embodiment the bentonite was pretreated by boiling in water (cooked clay) before addition to the tissue. A handsheet study was carried out to evaluate the utility of incorporating irritant sequestrants into tissue structures. Tissue prototypes were prepared in the laboratory from wood fibers (70% bahia SUL eucalyptus, 30% northern softwood kraft). In preparing the tissue sheets, a stock slurry was prepared from 50 grams (dry weight) of fiber and approximately 1950 g of distilled water for each prototype prepared. The stock slurry was then beaten in a British Pulp Disintegrator (Messmer Instruments Limited Part No. ME 295 Mark IIIC 1 mp; KC Item No.: 1071274) at 3000 rpm for five minutes. Two ml of 0.5% w/v Kymene (Product #557LX; Hercules Incorporated; Wilmington, Del.) was added to the resulting slurry. For handsheets that contained clay, 625 mg of bentonite was added in several increments with continuous stirring. Control handsheets were prepared without the addition of bentonite. The slurry was mixed for an additional 1–2 minutes following the final addition of clay. The resulting slurry was made up to 8 liters with distilled water. Then 225 mls of this diluted, well-mixed, slurry was used for making 8.5 inch$^2$ tissue sheets in a Valley Ironwork mold (Voith-Sulzer Papertech; KC Item No. 773193). The resulting sheets were then couched off the screen and pressed in a press with equipped blotter sheets at a pressure of 75 pounds per square inch for one minute. The wet sheets were dried over a steam dryer for two minutes, and then in an oven at about 100° C. to a constant dry weight (30 grams per square meter).

The amount of clay present in the tissue was determined by analytical methods. Pre-weighed samples of the tissue prototypes were burned over a Meker burner, heated in a Muffle furnace at 550° C. for 2 hours. The resulting ash was cooled and weighed. The clay material itself was treated similarly to account for weight loss attributed to water content or other volatiles lost during the heating process. The amount of ash present in control tissues devoid of clay was subtracted from the amount of ash present in the tissues with clay. The difference was attributed to the clay content. The amount of clay detected in the tissue prototypes was ranged between undetectable to 0.38%.

Tissue prototypes were evaluated for their ability to sequester the skin irritant IL-8 from 50 mM TRIS buffer @ pH 7.4 with 0.1% BSA and 150 mM NaCl. An IL-8 solution was prepared in this buffer at a target concentration of 50 ng/ml. This was accomplished by adding 100 $\mu$l of IL-8 solution for each mg of tissue placed in a 1.5 ml Eppendorf tube. Tubes containing test tissue, control tissue, or just buffer with IL-8 were incubated on a rocking platform for 90 minutes at room temperature. At the conclusion of the incubation period the tubes were centrifuged and the supernates analyzed for IL-8 remaining in solution. Sequestration of IL-8 was determined by comparing removal in control tissue to that observed in the buffer control and that realized in tubes containing test tissue.

The results (see FIG. 16) demonstrate that the addition of non-modified bentonite clay imparts to tissues an increased affinity for the skin irritant IL-8. Tissue without the inclusion of clay removed 5% of the IL-8 from solution. In contrast, the tissue with clay or cooked clay removed 82% and 92% of the IL-8 from solution, respectively.

Example #9

The Ability of Non-clay Sequestrants to Adsorb the Skin Irritant IL-8

The ability of silica and titanium dioxide ($TiO_2$) to remove skin irritants present in nasal secretions (IL-8) was evaluated using methods similar to those described above for the evaluation of clays. In this experiment fumed silica with a mean particle size of 7 nm (SIGMA #S-5130), silica with a mean particle size of 1 and 5 $\mu$m, and $TiO_2$ were evaluated. The ability of these materials to sequester IL-8 was determined in 50 mM TRIS buffer @ pH 7.4 with 0.1% BSA and 150 mM NaCl. An IL-8 solution was prepared in this buffer at a concentration of 35 ng/ml. Sequestration was determined by adding 100 $\mu$l of IL-8 solution for each mg of silica or $TiO_2$ placed in a 1.5 ml Eppendorf tube. Tubes containing test material or just buffer with IL-8 were incubated on a rocking platform for 60 minutes at room temperature. At the conclusion of the incubation period the tubes were centrifuged and the supernates analyzed for IL-8 remaining in solution. Sequestration of IL-8 was determined by comparing the amount of IL-8 in supernates derived from tubes containing test material to that present in the control tube devoid of sequestrant.

The results demonstrate (see FIG. 17) that both silica and $TiO_2$ have the ability to bind the skin irritant IL-8.

Example #10

Binding Kinetics of Skin Irritants (IL-8 and $PGE_2$) to Non-clay Sequestrants The ability of silica and titanium dioxide ($TiO_2$) to remove skin irritants present in nasal secretions (IL-8 and $PGE_2$) as a function of time was evaluated. The methods used to measure this was similar to those described above for the evaluation of irritant binding by silica and $TiO_2$ for a single 60 minute incubation. In this experiment, fumed silica with a mean particle size of 7 nm (SIGMA #S-5130), silica with a mean particle size of 1 and 5 μm, and $TiO_2$ were again evaluated. IL-8 and $PGE_2$ sequestration was determined in 50 mM TRIS buffer @ pH 7.4 with 0.1% BSA and 150 mM NaCl. An IL-8 solution was prepared in this buffer at a target concentration of 50 ng/ml.

Figure 18:
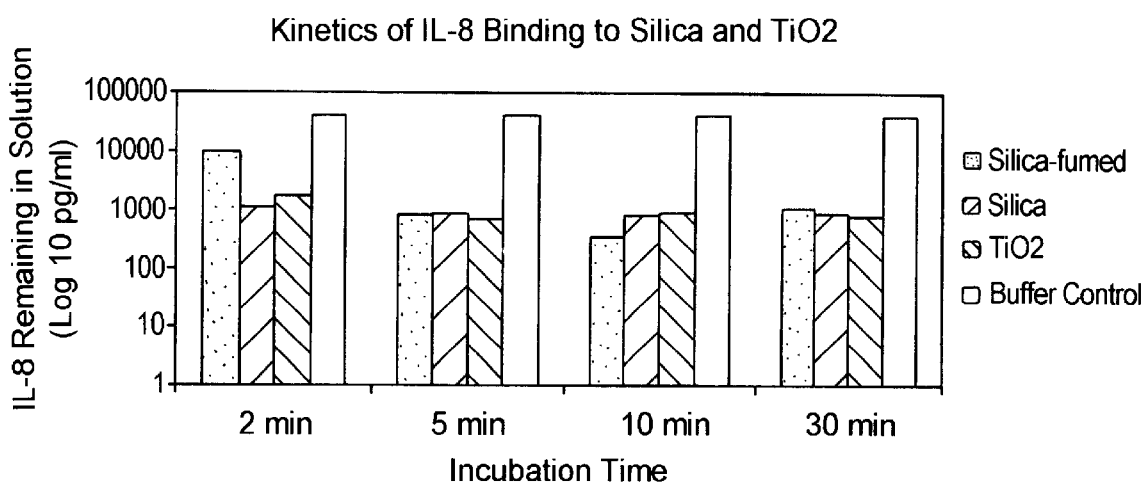
FIG. 18 shows the kinetics of skin irritant binding.

Similarly, a $PGE_2$ solution was prepared. Sequestration was determined by adding 100 μl of irritant solution for each mg of silica or $TiO_2$ placed in a 1.5 ml Eppendorf tube. Tubes containing test material or just buffer with IL-8 were incubated on a rocking platform for 2, 5, 10, and 30 minutes at room temperature. This procedure was performed in parallel for the evaluation of $PGE_2$ sequestration. At the conclusion of each incubation period tubes were centrifuged and the supernates analyzed for IL-8 or $PGE_2$ remaining in solution. Sequestration of IL-8 or $PGE_2$ was determined by comparing the amount of each analyte present in supernates derived from tubes containing test material to that present in the control tube devoid of sequestrant. The results for IL-8 sequestration are summarized in FIG. 18. Binding of $PGE_2$ to silica and $TiO_2$ was not detected (data not shown).

Table 2 demonstrates that binding of IL-8 to these sequestrants is rapid. The results demonstrate that both silica and $TiO_2$ have the ability to bind the skin irritant IL-8 (FIG. 18) and that this binding is rapid (Table 2). However, non-modified silica and $TiO_2$ do not have a detectable affinity for the relatively hydrophobic skin irritant $PGE_2$ present in nasal secretions (Data not shown).

TABLE #2

| Timepoint (minutes of incubation) | Fumed Silica IL-8 Remaining (pg/ml) | Silica IL-8 Remaining (pg/ml) | $TiO_2$ IL-8 Remaining (pg/ml) |
| --- | --- | --- | --- |
| Control | 44,891 | 44,891 | 44,891 |
| 2 | 9,755 | 1,135 | 1,816 |
| 5 | 866 | 920 | 732 |
| 10 | 375 | 827 | 972 |

The foregoing description of embodiments of the invention has been presented for purposes of illustration and description. It is not intended to be exhaustive or to limit the invention to the precise form disclosed. Obvious modifications or variations are possible in light of the above teachings. The embodiments were chosen and described to provide an illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

REFERENCES

1. Turner, R. B. et al 1998. Association Between Interleukin-8 Concentration in Nasal Secretions and Severity of Symptoms of Experimental Rhinovirus Colds. Clin. Infect. Dis. 26–840–846.
2. Roseler, S. et al 1995. Elevated levels of Interleukins IL-1β, IL-6, and IL-8 in Naturally Acquired Viral Rhinitis. Eur. Arch. Otolaryn. 252(Suppl. 1):S61–S63.
3. Bachert, C. et al 1995. Proinflammatory Cytokines in Allergic Rhinitis. Eur. Arch. Otolaryn. 252(Suppl. 1):S44–S49.
4. Baumgarten, W. J.-A. and Petersson, G. 1995. Contralateral Differences Among Biomarkers Determined by a Modified Nasal Lavage Technique after Unilateral Antigen Challenge. Allergy 50:308–315.
5. Howarth, P. H. 1997. Mediators of Nasal Blockage in Allergic Rhinitis. Allergy, 52(suppl. 40):12–18.
6. Smitz, W. D. et al. 1997. An Approach to the Understanding of the Nasal Early-Phase Reaction Induced by Nasal Allergen Challenge. Allergy, 52:162–167.
7. Togias, A. G. et al. 1985. Nasal Challenge with Cold, Dry Air Results in Release of Inflammatory Mediators. J. Clin. Invest. 76:1375–1381.
8. Knapp, H. R. and Murray, J. J. 1994. Leukotrienes as Mediators of Nasal Inflammation. Adv. Prostaglandin, Thromboxane, and Leukotriene Research, 22:279–288.
9. Short, S. M. 1995. Transport of Biologically Active Interferongamma Across Human Skin In Vitro. Pharm. Res. 12(8):1140–1145.
10. Greaves, M. W. and Camp, R. D. R. 1988. Prostaglandins, Leukotrienes, Phospholipase, Platelet Activating Factor, and Cytokines: An Integrated Approach to Inflammation of Human Skin. Arch Dermatol. Res. 280 [Suppl]:S33–S41.
11. Strange, P. et al. 1996. Staphylococcal Enterotoxin B Applied on Intact Normal and Intact Atopic Skin Induces Dermatitis. Arch. Dermatol. 132:27–33.
12. Schaefer, H. and Redelmeier, T. E. 1996. Relationship Between the Structure of Compounds and Their Diffusion Across Membranes. Pgs. 87–117. In Skin Barrier: Principles of Percutaneous Absorption. Karger, A G. Basel, Switzerland.
13. Distante, F. and Berardesca, E. 1995. Transepidermal Water Loss, Pgs. 1–4. In E. Berardesca (ed.), Bioengineering of the Skin: Methods and Instrumentation, CRC Press, Inc. Boca Raton, Fla.
14. Rougier, A., Lotte, C., and Maibach, H. 1989. In vivo Relationship Between Percutaneous Absorption and Transepidermal Water Loss, pgs. 175–190. In Bronaugh, R. L. and Maibach, H. I. (eds.), Percutaneous Absorption: Mechanisms-Methodology-Drug Delivery ($2^{nd}$ ed.). Marcel Dekker, Inc. New York, N.Y.
15. Lopez, S. et al. 1998. Profile of Women's Facial Skin for Transepidermal Water Loss, Temperature and Sebum Casual Level. Poster presented at the $12^{th}$ International Symposium on Bioengineering and the Skin. Boston, Jun. 25–27, 1998.
16. Wester, R. and Maibach, H. I. 1989. Regional Variation in Percutaneous Absorption. Pgs. 111–119. In Bronaugh, R. L. and Maibach, H. I. (eds.), Percutaneous Absorption: Mechanisms-Methodology-Drug Delivery ($2^{nd}$ ed.). Marcel Dekker, Inc. New York, N.Y.
17. Taljebini, M. et al. Cutaneous Permeability Barrier Repair Following Various Types of Insults: Kinetics and Effects of Occlusion. Skin Phamacol. 9:111–119.
18. Ueda, H. et al. 1996. Change in the Electrochemical Properties of Skin and the Lipid Packing in Stratum Corneum by Ultrasonic Radiation. Int. J. Pharm. 137:217–224.
19. Pliquett, U. and Weaver, C. 1996. Electroporation of Human Skin: Simultaneous Measurement of Changes in the Transport of Two Fluorescent Molecules and in the Passive Electrical Properties. Bioelectrochem. and Bioenerget. 39:1–12.
20. Patil, S. et al. 1996. Epidermal Enzymes as Penetration Enhancers in Transdermal Drug Delivery. J. Pharm. Sci. 85(3):249–252.

21. Menon, G. K., Feingold, K. R. and Elias, P. M. 1992. Lamellar Body Secretory Response to Barrier Disruption. J. Invest. Dermatol. 98:279–289.
2. Leveque, J. L. et al. 1993. How does Sodium Lauryl Sulfate Alter the Skin Barrier Function in Man? A Multiparametric Approach. Skin Pharmacol. 6:111–115.
23. Denda, M. et al. 1998. Exposure to a Dry Environment Enhances Epidermal Permeability Barrier Function. J. Invest. Dermatol. 111:858–863.
24. Frosh, P. J. and Kurte, A. 1994. Efficacy of Skin Barrier Creams (IV). The Repetitive Irritation Test (RIT) with a set of 4 Standard Irritants. Contact Dermatitis 31:161–168.
25. Treffel, P., Gabard, B. and Juch, R. 1994. Evaluation of Barrier Creams: An In vitro Technique on Human Skin. Acta Derm Venerol 74:7–11.
26. Malmsten, M. 1998. Formation of Adsorbed Protein Layers. J. Colloid and Interface Sci. 207:186–199.
27. Saaverda, S. S. and Lochmuller, C. H. 1988. The adsorption of Proteins on Chemically Modified Hydrophobic Surfaces. Pgs. 67–77. In Chemically Modified Surfaces In Science and Industry: Proceedings of the 10 Chemically Modified Surfaces Symposium (1987; Fort Collins, Colo.). Leyden, D. E. and Collins, W. T. eds. Gordon and Breach Science Publishers, New York, N.Y.
28. Tombacz, E. et al. 1998. Surface Modification of Clay Minerals by Organic Polyions. Colloids and Surfaces A: Physiochemical and Eng. Aspects 141:379–384.
29. Sullivan, E. J., Carey, J. W. and Bowman, R. S. 1998. Thermodynamics of Cationic Surfactant Sorption onto Natural Clinoptilolite. J. Colloid & Interface Sci. 206:369–380.
30. Biasci, L. et al. 1994. Functionalization of Montmorillonite by Methyl Methacrylate Polymers Containing Side Chain Ammino Cations. Polymer 35(15):3296–3309.
31. Kamyshny, A., Toledano, O., and Magdassi, S. 1999. Adsorption of hydrophobized IgG and Gelatin onto Phosphatidyl choline-coated Silica. Colloids and Surfaces B: Biointerfaces 13:187–194.
32. Atun, G. Hisarlt, G. and Tuncay, M. 1998. Adsorption of Safranine-O on Hydrophilic and Hydrophobic Glass Surfaces. Colloids and Surfaces A: Physiochemical and Eng. Aspects 143:27–33.
33. Parida, S. K. and Mishra, B. K. 1998. Adsorption of Styryl pyridinium dyes on Polyethylene-glycol-treated Silica. Colloids and Surfaces A: Physiochemical and Eng. Aspects 134:249–255.
34. Markowitz, M. A. et al. 1999. Surface Acidity and Basicity of Functionalized Silica Particles. Colloids and Surfaces A: Physiochemical and Eng. Aspects 150:85–94.
35. Kandori, K. et al. 1999. Adsorption of Bovine Serum Albumin and Lysozyme. on Hydrophobic Calcium Hydroxyapatites. J. Colloid & Interface Sci. 212:600–603.
36. Kandor, K. et al. 1999. Preparation and Characterization of Hydrophobic Calcium Hydroxyapatite Particles Grafting Oleylphosphate Groups. Colloids and Surfaces A: Physiochemical and Eng. Aspects 150:161–170.
37. Esumi, K. et al. 1998. Adsorption Characteristics of Cationic Surfactants on Titanium Dioxide with Quaternary Ammonium Groups and Their Adsolubilization. J. Colloid & Interface Sci. 202:377–384.

We claim:

1. A facial tissue comprising a facial tissue substrate, and an essentially anhydrous composition consisting essentially of a) a hydrophilic nasal secretion skin irritant sequestering agent that can bind a cytokine, the hydrophilic nasal secretion skin irritant sequestering agent being selected from an unmodified clay, silica, titanium dioxide, and combinations thereof; b) a hydrophobic nasal secretion skin irritant sequestering agent that can bind an eicosanoid, the hydrophobic nasal secretion skin irritant sequestering agent being selected from hydrophobically modified clay, hydrophobically modified silica, hydrophobically modified titanium dioxide, and combinations thereof; and optionally c) a vehicle selected from a gel paste, cream, powder, lotion, emulsion, aqueous formulation, and any combination thereof; and optionally d) a lipophilic skin health benefit agent.

2. The facial tissue of claim 1, wherein the hydrophilic and hydrophobic nasal secretion skin irritant sequestering agents are isolated from each other on discrete regions of the substrate.

3. The facial tissue of claim 2, wherein the discrete regions of the substrate are defined as separate layers of the substrate.

4. The facial tissue of claim 2, wherein the discrete regions of the substrate are defined as separate plies of the substrate.

5. The facial tissue of claim 2, wherein the discrete regions of the substrate are defined by a pattern configuration on the substrate.

6. The facial tissue of claim 2, wherein the discrete regions of the substrate are defined by separate fibers of the substrate.

7. The facial tissue of claim 1, wherein the tissue substrate comprises paper fibers.

8. The facial tissue of claim 1, wherein the cytokine is selected from interleukin-8, interleukin-1α, interleukin-1β, and combinations thereof.

9. The facial tissue of claim 1, wherein the eicosanoid comprises a prostaglandin.

10. The facial tissue of claim 9, wherein the prostaglandin comprises prostaglandin $E_2$.

11. The facial tissue of claim 1, wherein the eicosanoid comprises a leukotriene.

12. The facial tissue of claim 11, wherein the leukotriene comprises leukotriene $B_4$.

13. The facial tissue of claim 1, wherein the unmodified clay is selected from bentonite, kaolinite, laponite, zeolite, montmorillonite, beidellite, hectorite, saponite, stevensonite, and combinations thereof.

14. The facial tissue of claim 1, wherein the unmodified clay comprises bentonite.

15. The facial tissue of claim 1, wherein the hydrophilic nasal secretion skin irritant sequestering agent is present in the tissue in an amount of 0.001% to 5.0% by weight of the total weight of the facial tissue.

16. The facial tissue of claim 1, wherein the hydrophilic nasal secretion skin irritant sequestering agent is present in the tissue in an amount of 0.01% to 1.0% by weight of the total weight of the facial tissue.

17. The facial tissue of claim 1, wherein the hydrophobically modified clay comprises a quaternary ammonium modified bentonite.

18. The facial tissue of claim 1, wherein the hydrophobically modified clay comprises a quaternary ammonium modified montmorillonite.

19. The facial tissue of claim 1, wherein the hydrophobic nasal secretion skin irritant sequestering agent is present in the tissue in an amount of 0.001% to 5.0% by weight of the total weight of the facial tissue.

20. The facial tissue of claim 1, wherein the hydrophobic nasal secretion skin irritant sequestering agent is present in the tissue in an amount of 0.01% to 1.0% by weight of the total weight of the facial tissue.

21. The facial tissue of claim 1, wherein the skin irritants are bound to the sequestering agents present on the substrate.

22. The facial tissue of claim 1, wherein the skin irritants are bound to the sequestering agents present on skin.

23. The facial tissue of claim 1, wherein the lipophilic skin health benefit agent has an average hydrocarbon chain length greater than C-8.

24. The facial tissue of claim 1, wherein the lipophilic skin health benefit agent is selected from stearic acid, isoparaffin, petrolatum, and any combination thereof.

25. The facial tissue of claim 1, wherein the lipophilic skin health benefit agent is selected from fatty acid, fatty acid esters, fatty alcohol, triglyceride, phospholipid, mineral oil, essential oil, sterol, sterol ester, emollients, waxes, and any combination thereof.

* * * * *